United States Patent
Patel et al.

(10) Patent No.: US 11,504,124 B2
(45) Date of Patent: Nov. 22, 2022

(54) SURGICAL INSTRUMENT WITH LOCKOUT MECHANISM

(71) Applicant: Intuitive Surgical Operations, Inc., Sunnyvale, CA (US)

(72) Inventors: Atal C. Patel, Mission Viejo, CA (US); Charles N. Godin, Palo Alto, CA (US); Matthew Wixey, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 182 days.

(21) Appl. No.: 17/104,223

(22) Filed: Nov. 25, 2020

(65) Prior Publication Data

US 2021/0077101 A1 Mar. 18, 2021

Related U.S. Application Data

(63) Continuation of application No. 16/205,128, filed on Nov. 29, 2018, now Pat. No. 10,863,988.

(Continued)

(51) Int. Cl.
*A61B 17/072* (2006.01)
*A61B 17/295* (2006.01)
*A61B 17/29* (2006.01)

(52) U.S. Cl.
CPC ...... *A61B 17/07207* (2013.01); *A61B 17/295* (2013.01); *A61B 2017/07257* (2013.01);
(Continued)

(58) Field of Classification Search
CPC ............ A61B 17/295; A61B 17/07207; A61B 17/068
See application file for complete search history.

(56) References Cited

U.S. PATENT DOCUMENTS

| 4,305,539 A | 12/1981 | Korolkov et al. |
| 4,319,576 A | 3/1982 | Rothfuss |

(Continued)

FOREIGN PATENT DOCUMENTS

| EP | 0277532 B1 | 8/1990 |
| EP | 0277529 B1 | 4/1993 |

(Continued)

OTHER PUBLICATIONS

International Search Report and Written Opinion for Application No. PCT/US2020/054568, dated Jan. 29, 2021, 13 pages.

(Continued)

*Primary Examiner* — Nathaniel C Chukwurah
(74) *Attorney, Agent, or Firm* — Farber LLC

(57) ABSTRACT

Drive assemblies for surgical clamping and cutting instruments, as well as surgical clamping and cutting instruments using these drive assemblies, are disclosed. The drive assemblies may include a drive member, a locking member mounted to the drive member, and a spring. The drive member may be configured to releasably engage at least one of a knife or a shuttle of a surgical clamping and cutting instrument for translating the knife and/or shuttle in a distal direction through a firing stroke. The locking member may be movable from a first position permitting distal translation of the drive member through the firing stroke, and a second position inhibiting distal translation of the drive member through the firing stroke. The spring may be configured to bias the locking member toward the second position.

20 Claims, 18 Drawing Sheets

Related U.S. Application Data

(60) Provisional application No. 62/592,330, filed on Nov. 29, 2017.

(52) U.S. Cl.
CPC ............... *A61B 2017/07271* (2013.01); *A61B 2017/07285* (2013.01); *A61B 2017/2946* (2013.01)

(56) References Cited

U.S. PATENT DOCUMENTS

| | | |
|---|---|---|
| 4,429,695 A | 2/1984 | Green |
| 4,509,518 A | 4/1985 | McGarry et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,767,044 A | 8/1988 | Green |
| 4,809,695 A | 3/1989 | Gwathmey et al. |
| 4,848,637 A | 7/1989 | Pruitt |
| 4,892,244 A | 1/1990 | Fox et al. |
| 4,930,503 A | 6/1990 | Pruitt |
| 4,978,049 A | 12/1990 | Green |
| 5,027,834 A | 7/1991 | Pruitt |
| 5,040,715 A | 8/1991 | Green et al. |
| 5,133,735 A | 7/1992 | Slater et al. |
| 5,133,736 A | 7/1992 | Bales, Jr. et al. |
| 5,180,092 A | 1/1993 | Crainich |
| 5,275,323 A | 1/1994 | Schulze et al. |
| 5,307,976 A | 5/1994 | Olson et al. |
| 5,312,023 A | 5/1994 | Green et al. |
| 5,334,183 A | 8/1994 | Wuchinich |
| 5,342,396 A | 8/1994 | Cook |
| 5,366,133 A | 11/1994 | Geiste |
| 5,452,836 A | 9/1995 | Huitema et al. |
| 5,452,837 A | 9/1995 | Williamson, IV et al. |
| 5,480,089 A | 1/1996 | Blewett |
| 5,484,095 A | 1/1996 | Green et al. |
| 5,484,451 A | 1/1996 | Akopov et al. |
| 5,487,500 A | 1/1996 | Knodel et al. |
| 5,497,931 A | 3/1996 | Nakamura |
| 5,533,521 A | 7/1996 | Granger |
| 5,540,375 A | 7/1996 | Bolanos et al. |
| 5,554,164 A | 9/1996 | Wilson et al. |
| 5,560,530 A | 10/1996 | Bolanos et al. |
| 5,562,239 A | 10/1996 | Boiarski et al. |
| 5,571,116 A | 11/1996 | Bolanos et al. |
| 5,571,285 A | 11/1996 | Chow et al. |
| 5,615,820 A | 4/1997 | Viola |
| 5,624,452 A | 4/1997 | Yates |
| 5,628,446 A | 5/1997 | Geiste et al. |
| 5,652,849 A | 7/1997 | Conway et al. |
| 5,667,626 A | 9/1997 | Cayford et al. |
| 5,676,674 A | 10/1997 | Bolanos et al. |
| 5,688,269 A | 11/1997 | Newton et al. |
| 5,690,269 A | 11/1997 | Bolanos et al. |
| 5,693,042 A | 12/1997 | Boiarski et al. |
| 5,697,542 A | 12/1997 | Knodel et al. |
| 5,709,680 A | 1/1998 | Yates et al. |
| 5,752,644 A | 5/1998 | Bolanos et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,792,135 A | 8/1998 | Madhani et al. |
| 5,820,009 A | 10/1998 | Melling et al. |
| 5,826,776 A | 10/1998 | Schulze et al. |
| 5,833,695 A | 11/1998 | Yoon |
| 5,865,361 A | 2/1999 | Milliman et al. |
| 5,871,135 A | 2/1999 | Williamson, IV et al. |
| 5,911,353 A | 6/1999 | Bolanos et al. |
| 5,915,616 A | 6/1999 | Viola et al. |
| 5,941,442 A | 8/1999 | Geiste et al. |
| 5,954,259 A | 9/1999 | Viola et al. |
| 5,959,892 A | 9/1999 | Lin et al. |
| 6,032,849 A | 3/2000 | Mastri et al. |
| 6,079,606 A | 6/2000 | Milliman et al. |
| 6,174,309 B1 | 1/2001 | Wrublewski et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,330,956 B1 | 12/2001 | Willinger |
| 6,330,965 B1 | 12/2001 | Milliman et al. |
| 6,488,196 B1 | 12/2002 | Fenton, Jr. |
| 6,503,259 B2 | 1/2003 | Huxel et al. |
| 6,585,735 B1 | 7/2003 | Frazier et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,786,382 B1 | 9/2004 | Hoffman |
| 6,817,974 B2 | 11/2004 | Cooper et al. |
| 6,877,647 B2 | 4/2005 | Green et al. |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,114,642 B2 | 10/2006 | Whitman |
| 7,128,253 B2 | 10/2006 | Mastri et al. |
| 7,140,527 B2 | 11/2006 | Ehrenfels et al. |
| 7,140,528 B2 | 11/2006 | Shelton, IV et al. |
| 7,308,998 B2 | 12/2007 | Mastri et al. |
| 7,328,828 B2 | 2/2008 | Ortiz et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,455,676 B2 | 11/2008 | Holsten et al. |
| 7,472,814 B2 | 1/2009 | Mastri et al. |
| 7,481,349 B2 | 1/2009 | Holsten et al. |
| 7,494,039 B2 | 2/2009 | Racenet et al. |
| 7,565,993 B2 | 7/2009 | Milliman et al. |
| 7,588,174 B2 | 9/2009 | Holsten et al. |
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |
| 7,832,611 B2 | 11/2010 | Boyden et al. |
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,348,127 B2 | 1/2013 | Marczyk |
| 8,365,972 B2 | 2/2013 | Aranyi et al. |
| 8,371,492 B2 | 2/2013 | Aranyi et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,939 B2 | 3/2014 | Garrison |
| 8,783,541 B2 | 7/2014 | Shelton, IV et al. |
| 8,800,841 B2 | 8/2014 | Ellerhorst et al. |
| 8,858,547 B2 | 10/2014 | Brogna |
| 8,905,287 B2 | 12/2014 | Racenet et al. |
| 8,925,785 B2 | 1/2015 | Holsten et al. |
| 9,010,606 B2 | 4/2015 | Aranyi et al. |

(56) References Cited

U.S. PATENT DOCUMENTS

| | | |
|---|---|---|
| 9,055,961 B2 | 6/2015 | Manzo et al. |
| 9,192,378 B2 | 11/2015 | Aranyi et al. |
| 9,192,379 B2 | 11/2015 | Aranyi et al. |
| 9,216,019 B2 | 12/2015 | Schmid et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |
| 9,936,949 B2 | 4/2018 | Measamer et al. |
| 10,111,659 B2 | 10/2018 | Racenet et al. |
| 10,231,732 B1 | 3/2019 | Racenet et al. |
| 10,285,693 B2 | 5/2019 | Kimsey et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 2002/0165562 A1 | 11/2002 | Grant et al. |
| 2003/0181910 A1 | 9/2003 | Dycus et al. |
| 2004/0232195 A1 | 11/2004 | Shelton, IV et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0070925 A1 | 3/2005 | Shelton, IV et al. |
| 2005/0070958 A1 | 3/2005 | Swayze et al. |
| 2005/0178813 A1 | 8/2005 | Swayze et al. |
| 2005/0187576 A1 | 8/2005 | Whitman et al. |
| 2006/0000868 A1 | 1/2006 | Shelton, IV et al. |
| 2006/0016853 A1 | 1/2006 | Racenet |
| 2006/0022014 A1 | 2/2006 | Shelton, IV et al. |
| 2006/0022015 A1 | 2/2006 | Shelton et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0161190 A1 | 7/2006 | Gadberry et al. |
| 2006/0190031 A1 | 8/2006 | Wales et al. |
| 2006/0226196 A1 | 10/2006 | Hueil et al. |
| 2007/0010838 A1 | 1/2007 | Shelton, IV et al. |
| 2007/0045379 A1 | 3/2007 | Shelton, IV |
| 2007/0262116 A1 | 11/2007 | Hueil et al. |
| 2008/0023522 A1 | 1/2008 | Olson et al. |
| 2008/0078804 A1 | 4/2008 | Shelton et al. |
| 2009/0277947 A1 | 11/2009 | Viola |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2011/0022078 A1 | 1/2011 | Hinman |
| 2011/0174863 A1 | 7/2011 | Shelton, IV et al. |
| 2011/0251612 A1 | 10/2011 | Faller et al. |
| 2011/0251613 A1 | 10/2011 | Guerra et al. |
| 2011/0290854 A1 | 12/2011 | Timm et al. |
| 2011/0295270 A1 | 12/2011 | Giordano et al. |
| 2012/0022584 A1 | 1/2012 | Donnigan et al. |
| 2012/0071891 A1 | 3/2012 | Itkowitz et al. |
| 2012/0223121 A1 | 9/2012 | Viola et al. |
| 2013/0015231 A1 | 1/2013 | Kostrzewski |
| 2013/0056521 A1 | 3/2013 | Swensgard |
| 2013/0068821 A1 | 3/2013 | Huitema et al. |
| 2013/0087599 A1 | 4/2013 | Krumanaker et al. |
| 2013/0098965 A1 | 4/2013 | Kostrzewski et al. |
| 2013/0148577 A1 | 6/2013 | Terry et al. |
| 2013/0248577 A1 | 9/2013 | Leimbach et al. |
| 2013/0296922 A1 | 11/2013 | Allen, IV et al. |
| 2014/0001236 A1 | 1/2014 | Shelton, IV et al. |
| 2014/0025071 A1 | 1/2014 | Sims et al. |
| 2014/0175152 A1 | 6/2014 | Hess et al. |
| 2014/0180286 A1 | 6/2014 | Marczyk et al. |
| 2014/0263546 A1 | 9/2014 | Aranyi |
| 2014/0263559 A1 | 9/2014 | Williams et al. |
| 2014/0263567 A1* | 9/2014 | Williams ......... A61B 17/07207 227/180.1 |
| 2014/0263569 A1 | 9/2014 | Williams et al. |
| 2014/0343550 A1 | 11/2014 | Faller et al. |
| 2015/0209037 A1 | 7/2015 | Kostrzewski et al. |
| 2015/0250530 A1 | 9/2015 | Manzo et al. |
| 2015/0256609 A1 | 9/2015 | Morton et al. |
| 2015/0272576 A1 | 10/2015 | Cappola |
| 2015/0297227 A1 | 10/2015 | Huitema et al. |
| 2016/0038227 A1 | 2/2016 | Garrison |
| 2016/0120544 A1 | 5/2016 | Shelton, IV et al. |
| 2016/0175033 A1 | 6/2016 | Le |
| 2016/0192999 A1 | 7/2016 | Stulen et al. |
| 2016/0235489 A1 | 8/2016 | Gombert et al. |
| 2016/0270780 A1 | 9/2016 | Hall et al. |
| 2016/0287251 A1 | 10/2016 | Shelton, IV et al. |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0079710 A1 | 3/2017 | Deville et al. |
| 2017/0097035 A1 | 4/2017 | Zimmerman et al. |
| 2017/0135746 A1 | 5/2017 | Tetzlaff et al. |
| 2017/0189028 A1 | 7/2017 | Aranyi |
| 2017/0245857 A1 | 8/2017 | Shelton, IV et al. |
| 2017/0296172 A1 | 10/2017 | Harris et al. |
| 2018/0021042 A1 | 1/2018 | Nicholas et al. |
| 2018/0161052 A1 | 6/2018 | Weir et al. |
| 2018/0168581 A1 | 6/2018 | Hunter et al. |
| 2018/0168622 A1 | 6/2018 | Shelton, IV et al. |
| 2018/0168628 A1 | 6/2018 | Hunter et al. |
| 2018/0168641 A1 | 6/2018 | Harris et al. |
| 2018/0168642 A1 | 6/2018 | Shelton, IV et al. |
| 2018/0168649 A1 | 6/2018 | Shelton, IV et al. |
| 2018/0310948 A1 | 11/2018 | Stamm et al. |
| 2019/0000454 A1 | 1/2019 | Swayze et al. |
| 2019/0015124 A1 | 1/2019 | Williams et al. |
| 2019/0125347 A1 | 5/2019 | Stokes et al. |
| 2019/0142531 A1 | 5/2019 | Wentworth et al. |
| 2019/0231350 A1 | 8/2019 | Scott et al. |
| 2019/0290374 A1 | 9/2019 | Ramadorai |
| 2019/0365458 A1 | 12/2019 | Whitlock et al. |
| 2020/0397430 A1 | 12/2020 | Patel et al. |
| 2021/0000557 A1 | 1/2021 | Mustufa et al. |
| 2021/0022736 A1 | 1/2021 | Wixey |
| 2021/0177495 A1 | 6/2021 | Ross et al. |
| 2021/0177500 A1 | 6/2021 | Khalaji |
| 2021/0212683 A1 | 7/2021 | Burbank |
| 2021/0386427 A1 | 12/2021 | Millman et al. |
| 2022/0015762 A1 | 1/2022 | Wixey et al. |
| 2022/0015763 A1 | 1/2022 | Wixey et al. |
| 2022/0015823 A1 | 1/2022 | Wilson et al. |
| 2022/0054130 A1 | 2/2022 | Overmyer et al. |
| 2022/0061836 A1 | 3/2022 | Parihar et al. |
| 2022/0061840 A1 | 3/2022 | Hites |
| 2022/0061841 A1 | 3/2022 | Wixey et al. |
| 2022/0071632 A1 | 3/2022 | Patel et al. |
| 2022/0079585 A1 | 3/2022 | Egan |
| 2022/0160358 A1 | 5/2022 | Wixey |
| 2022/0183686 A1 | 6/2022 | Wixey et al. |

FOREIGN PATENT DOCUMENTS

| | | |
|---|---|---|
| EP | 1090592 A1 | 4/2001 |
| EP | 1728473 A1 | 12/2006 |
| EP | 1479346 B1 | 1/2007 |
| EP | 1621141 B1 | 7/2007 |
| EP | 1316290 B1 | 2/2012 |
| EP | 1754445 B1 | 10/2013 |
| EP | 3135225 A2 | 3/2017 |
| EP | 3158947 A1 | 4/2017 |
| EP | 3173029 A1 | 5/2017 |
| FR | 2828952 B1 | 12/2005 |
| JP | 5301166 B2 | 9/2013 |
| JP | 2016508792 A | 3/2016 |
| JP | 2016513570 A | 5/2016 |
| JP | 2017527396 A | 9/2017 |
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |

(56) References Cited

FOREIGN PATENT DOCUMENTS

| | | | |
|---|---|---|---|
| SU | 1442191 | A1 | 12/1988 |
| SU | 1459659 | A1 | 2/1989 |
| WO | WO-8602254 | A1 | 4/1986 |
| WO | WO-9005489 | A1 | 5/1990 |
| WO | WO-9734533 | A1 | 9/1997 |
| WO | WO-03094743 | A1 | 11/2003 |
| WO | WO-03094746 | A1 | 11/2003 |
| WO | WO-03094747 | A1 | 11/2003 |
| WO | WO-2012142872 | A1 | 10/2012 |
| WO | WO-2014106275 | A1 | 7/2014 |
| WO | WO-2017034803 | A2 | 3/2017 |
| WO | WO-2017156070 | A1 | 9/2017 |
| WO | WO-2017214243 | A1 | 12/2017 |
| WO | WO-2018005750 | A1 | 1/2018 |
| WO | WO-2018071497 | A1 | 4/2018 |
| WO | WO-2018118402 | A1 | 6/2018 |

OTHER PUBLICATIONS

International Preliminary Reporton Patentability for Application No. PCT/US2019/019501, dated Sep. 3, 2020, 7 pages.
International Search Report and Written Opinion for Application No. PCT/US19/17646, dated Apr. 16, 2019, 11 pages.
International Search Report and Written Opinion for Application No. PCT/US2019/056979, dated Dec. 18, 2019, 8 pages.
International Search Report and Written Opinion for Application No. PCT/US2019/062344, dated Mar. 23, 2020, 17 pages.
International Search Report and Written Opinion for Application No. PCT/US2019/062768, dated Mar. 9, 2020, 15 pages.
International Search Report and Written Opinion for Application No. PCT/US2019/064861, dated Mar. 30, 2020, 18 pages.
International Search Report and Written Opinion for Application No. PCT/US2019/066513, dated Apr. 21, 2020, 8 pages.
International Search Report and Written Opinion for Application No. PCT/US2019/066530, dated Apr. 21, 2020, 8 pages.
International Search Report and Written Opinion for Application No. PCT/US2020/020672, dated Jun. 29, 2020, 10 pages.
International Search Report and Written Opinion for Application No. PCT/US2020/033481, dated Sep. 3, 2020, 22 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Search Report and Written Opinion for Application No. PCT/US2021/012284, dated May 6, 2021, 23 pages.
European Search Report (Corrected version) for Application No. EP19750317.0, dated Mar. 28, 2022, 26 pages.
International Preliminary Report on Patentability for Application No. PCT/US2019/017646, dated Aug. 27, 2020, 10 pages.
International Search Report and Written Opinion for Application No. POT/US2020/025655, dated Jul. 22, 2020, 8 pages.
International Search Report and Written Opinion for Application No. PCT/US2019/019501, dated May 9, 2019, 8 pages.
Partial European Search Report for Application No. EP19757451.0, dated Feb. 2, 2022, 12 pages.

\* cited by examiner

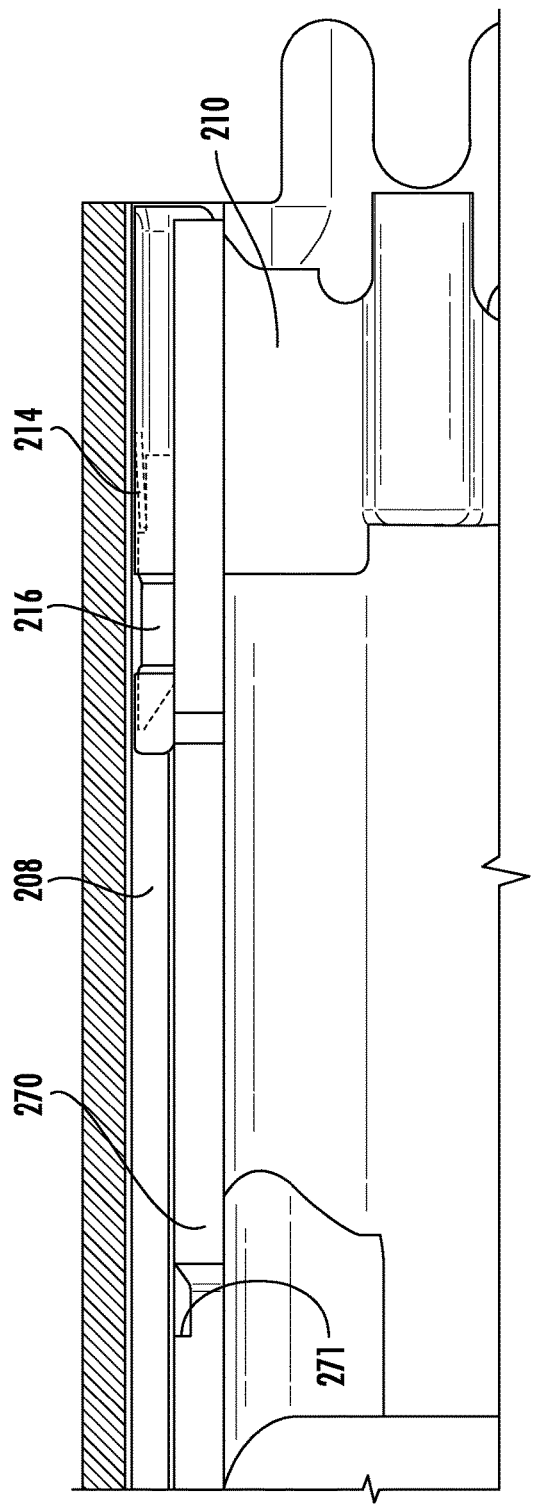
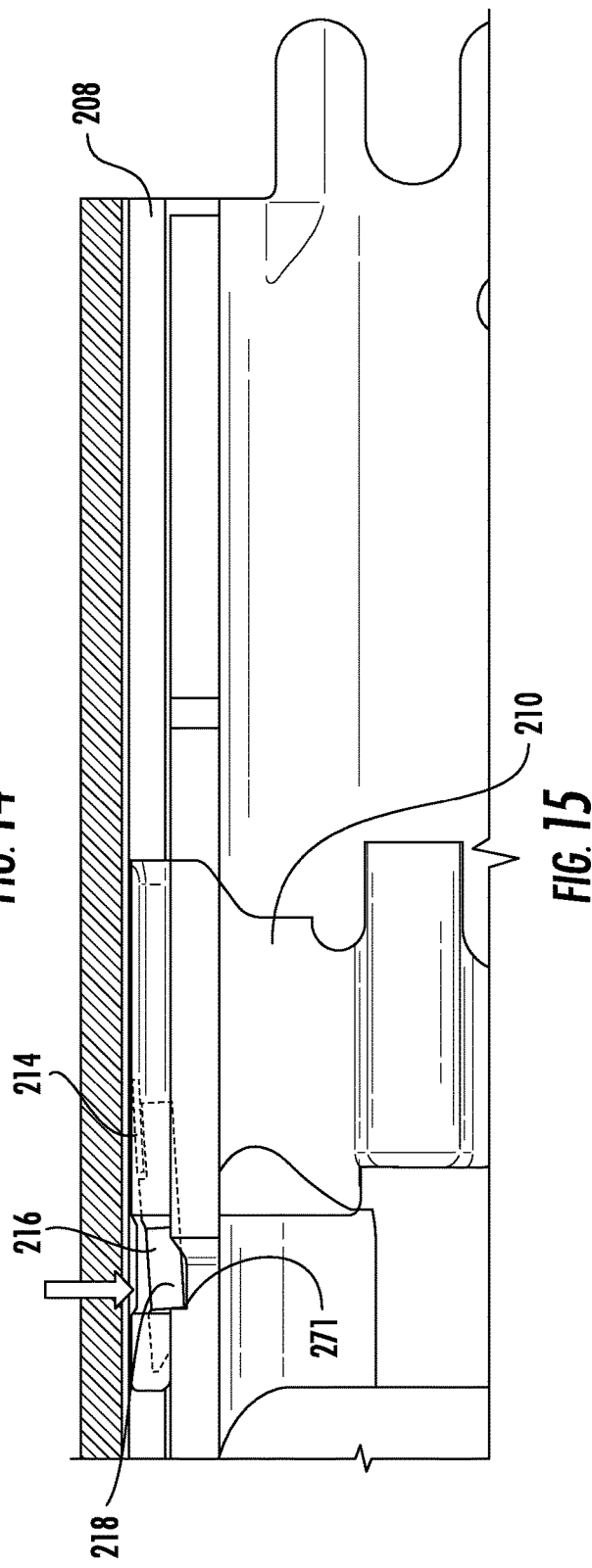
FIG. 14
FIG. 15

SURGICAL INSTRUMENT WITH LOCKOUT MECHANISM

CROSS-REFERENCE TO RELATED APPLICATIONS

This application is a Continuation of U.S. Nonprovisional application Ser. No. 16/205,128, filed Nov. 29, 2018, which claims the benefit of U.S. Provisional Application No. 62/592,330, filed on Nov. 29, 2017, the entire contents of each are incorporated herein by reference.

BACKGROUND

1. Technical Field

The present disclosure relates to surgical clamping and cutting instruments having a locking mechanism to prevent firing of the instruments.

2. Background of the Related Art

Surgical clamping and cutting instruments, such as, for example, surgical stapling instruments, may include an end effector having opposing jaws that clamp tissue and a knife that cuts the clamped tissue. It is often advantageous for an end effector of a surgical stapling instrument to be reusable. To that end, staple cartridges can be fitted into one jaw of the end effector prior to each use of the surgical stapling instrument.

It is desirable to prevent firing of a surgical stapling instrument while a spent cartridge remains in place on the jaw. Thus, a need exists for effective mechanisms to prevent firing of a surgical stapling instrument while a spent staple cartridge is in place in the end effector of the surgical stapling instrument.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure relates to improved surgical stapling instruments having a locking mechanism. Surgical stapling instruments described herein employ a proximal to distal knife movement, thereby orienting the knife to greatly reduce the likelihood of unintentionally cutting tissue while removing the surgical instrument from the surgical site. The surgical stapling instrument has a locking mechanism to prevent hazardous actuation of a knife or drive beam when there is a spent or previously fired cartridge in place.

In one aspect, a drive assembly for use with a surgical stapling instrument is provided, which drive assembly includes a drive member configured to releasably engage and translate at least one of a knife or a shuttle of a stapling instrument in a distal direction through a staple firing stroke. A locking member is mounted to the drive member and movable from a first position permitting distal translation of the drive member through the staple firing stroke, to a second position inhibiting distal translation of the drive member through the staple firing stroke. A spring is configured to bias the locking member toward the second position.

In another aspect, a surgical stapling instrument is provided, which surgical stapling instrument includes an anvil jaw assembly, and a staple jaw assembly, including a knife. A drive member is configured to releasably engage the knife, the knife disengaging from the drive member upon subsequent distal movement of the drive member. The surgical stapling instrument further includes a locking member supported by the drive member and being pivotable from a first position permitting distal translation of the drive member, to a second position preventing distal translation of the drive member. The knife, when proximally positioned, releasably engages the locking member to maintain the locking member in the first position, the knife disengaging from the locking member after the drive member has been driven distally. A slot is configured to engage the locking member when the locking member is in the second position.

In another aspect, a surgical stapling instrument is provided, which surgical stapling instrument includes an anvil jaw assembly, and a staple jaw assembly, including a knife. A drive member is configured to releasably engage a shuttle, the shuttle disengaging from the drive member upon subsequent distal movement of the drive member. The surgical stapling instrument further includes a locking member supported by the drive member and being pivotable from a first position permitting distal translation of the drive member, to a second position preventing distal translation of the drive member. The shuttle, when proximally positioned, releasably engages the locking member to maintain the locking member in the first position, the shuttle disengaging from the locking member after the drive member has been driven distally. A slot is configured to engage the locking member when the locking member is in the second position.

BRIEF DESCRIPTION OF THE DRAWINGS

The above and other aspects, features, and advantages of the present disclosure will become more apparent in light of the following detailed description when taken in conjunction with the accompanying drawings in which:

FIGS. 12-14 are a partial side, cross-sectional views of a surgical stapling instrument of FIG. 9 with the jaws of the end effector in the closed position showing sequential stages of proximal movement of the drive assembly after completion of a firing stroke and ejection of staples from the staple cartridge;

FIG. 15 is a partial side, cross-sectional view of a surgical stapling instrument of FIG. 9 with the jaws of the end effector in the closed position with a spent cartridge in place in the lower jaw assembly, thereby activating the lockout mechanism;

DETAILED DESCRIPTION

Particular embodiments of the present surgical stapling instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in unnecessary detail.

The present disclosure relates to drive assemblies including a drive member, a locking member mounted to the drive member, and a spring. The drive member is configured to releasably engage at least one of a knife or a shuttle of a surgical stapling instrument and to translate the knife and/or shuttle in a distal direction through a staple firing stroke. Contact between the drive member and the knife and/or shuttle is releasable in that once the knife and/or shuttle are translated by the drive member in the distal direction through a staple firing stroke, the knife and/or shuttle disengages from the drive member, remains at a distal portion of the stapling instrument, and is not translated in a proximal direction by the drive member. The locking member is movable from a first position permitting distal translation of the drive member through the staple-firing stroke, and a second position inhibiting distal translation of the drive member through the staple firing stroke. The spring is configured to bias the locking member toward the second position.

While the following disclosure is presented with respect to a linear surgical stapler where staples are sequentially fired, it should be understood that the present drive assemblies may be readily adapted for use in any type of surgical clamping and cutting instruments, whether or not the surgical clamping and cutting instrument applies a fastener. The surgical clamping and cutting instrument may be a minimally invasive (e.g., laparoscopic) instrument or an instrument used for open surgery.

Additionally, the present drive assemblies may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

Figure 1A:
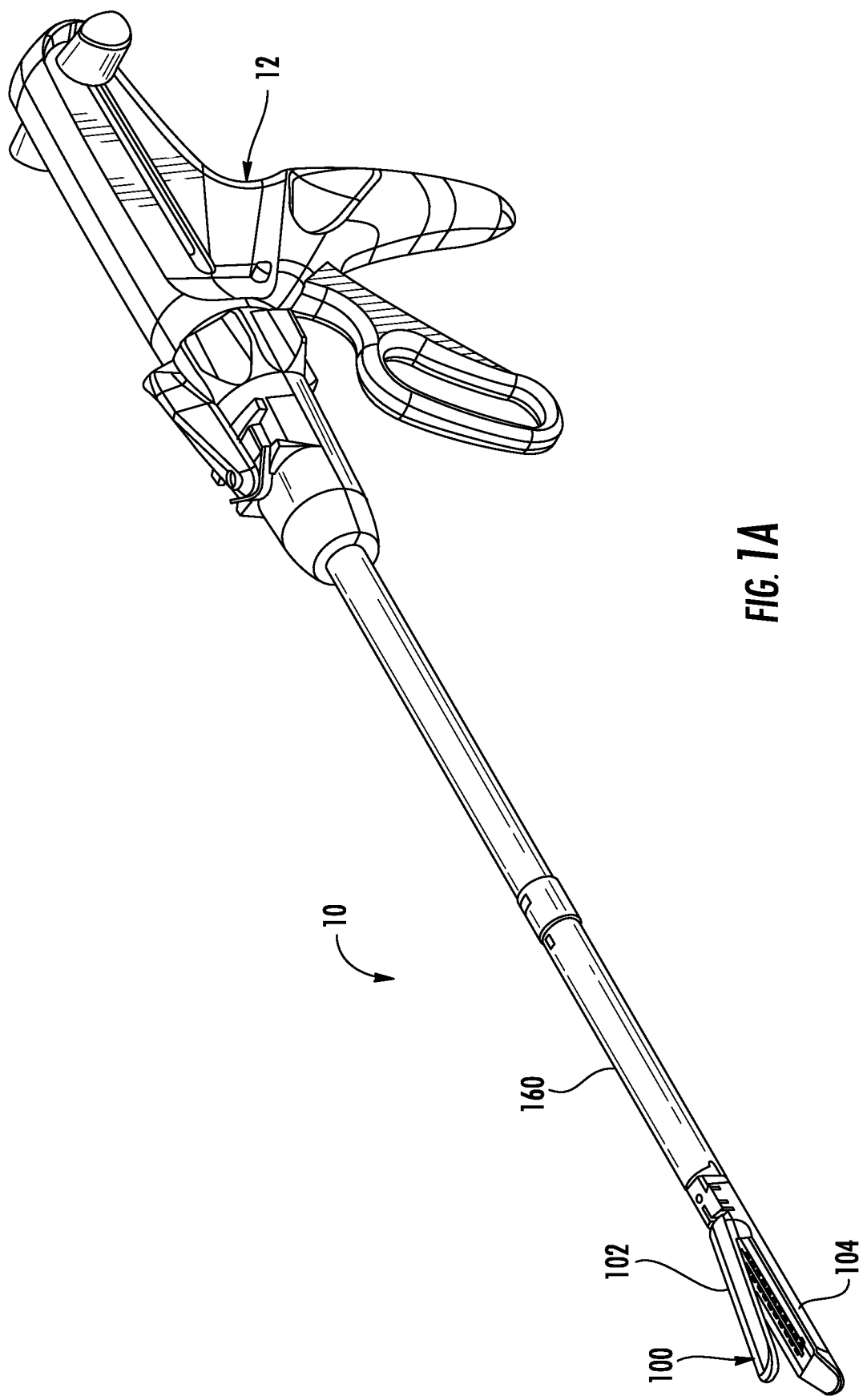
FIG. 1A is a perspective view of an illustrative surgical stapling instrument.

FIG. 1A is a perspective view of an illustrative surgical stapling instrument 10 capable of utilizing a drive assembly and locking mechanism in accordance with the present disclosure. Surgical stapling instrument 10 includes a handle assembly 12, and an end effector 100 including an anvil jaw assembly 102 and a staple jaw assembly 104 mounted on an elongated shaft 160 of the surgical stapling instrument 10.

Figure 1B:
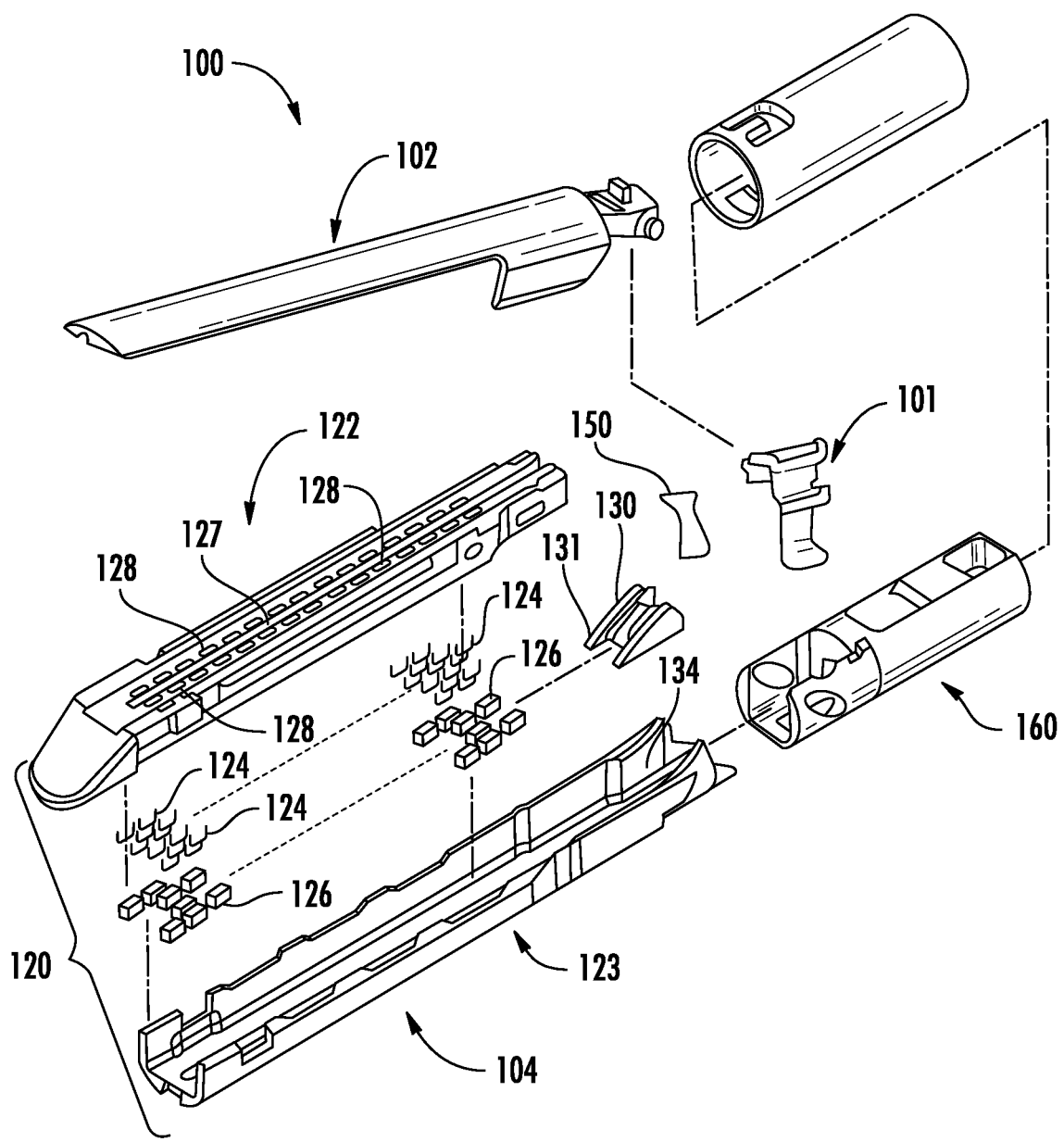
FIG. 1B is an exploded view of an illustrative end effector of a surgical stapling instrument.

FIG. 1B shows anvil jaw assembly 102, including an anvil 106 having staple forming pockets 103 (see FIG. 3A) supported thereon, and staple jaw assembly 104. Staple jaw assembly 104 and anvil jaw assembly 102 are configured to move from an open position to a closed position. In the open position, a fresh stapling cartridge can be loaded into jaw assembly 104, a spent staple cartridge removed from jaw assembly 104, and tissue may be positioned between the jaw assemblies 102, 104. In the closed position, jaw assemblies 102, 104 cooperate to close upon and clamp tissue such that cartridge 122 and anvil 106 are in close cooperative alignment. In the embodiment shown in FIGS. 1A and 1B, staple jaw assembly 104 is stationary and anvil jaw assembly 102 pivots to the open position. In other embodiments illustrated herein, the jaw assembly containing the anvil is stationary and the jaw assembly containing the staple cartridge pivots to the open position. As those skilled in the art reading this disclosure will appreciate, in yet other embodiments both the anvil jaw assembly and the staple jaw assembly may pivot.

With continued reference to FIG. 1B, staple jaw assembly 104 includes a staple cartridge 122 supported in a channel 134 on jaw 123. Cartridge 122 includes a plurality of staples 124 that are supported on corresponding staple drivers 126 provided within respective staple apertures 128 formed in cartridge 122. Cartridge 122 also includes a shuttle 130 having an inclined distal portion 131 that, upon distal movement, sequentially acts on staple drivers 126, camming them upwardly thereby moving staples 124 into deforming contact with anvil 106. Cartridge 122 also includes a knife 150 configured to translate distally through a channel 127 in cartridge 122 and sever clamped, stapled tissue.

FIG. 1B further shows a drive assembly 101 that is movably supported on the surgical stapling instrument such that it may pass distally through cartridge 122 and staple jaw assembly 104 when the surgical stapling instrument is fired (e.g., actuated).

For a more detailed description of illustrative end effectors, reference may be made to U.S. Pat. Nos. 6,669,073 and 8,800,841, the entire contents of which are incorporated herein by this reference. It should of course, be understood that end effector shown in FIGS. 1A and 1B is merely illustrative, and that other end effectors may be employed, including but not limited to the end effectors shown in WO2014/106275, the entire contents of which are incorporated herein by this reference.

Figure 2:
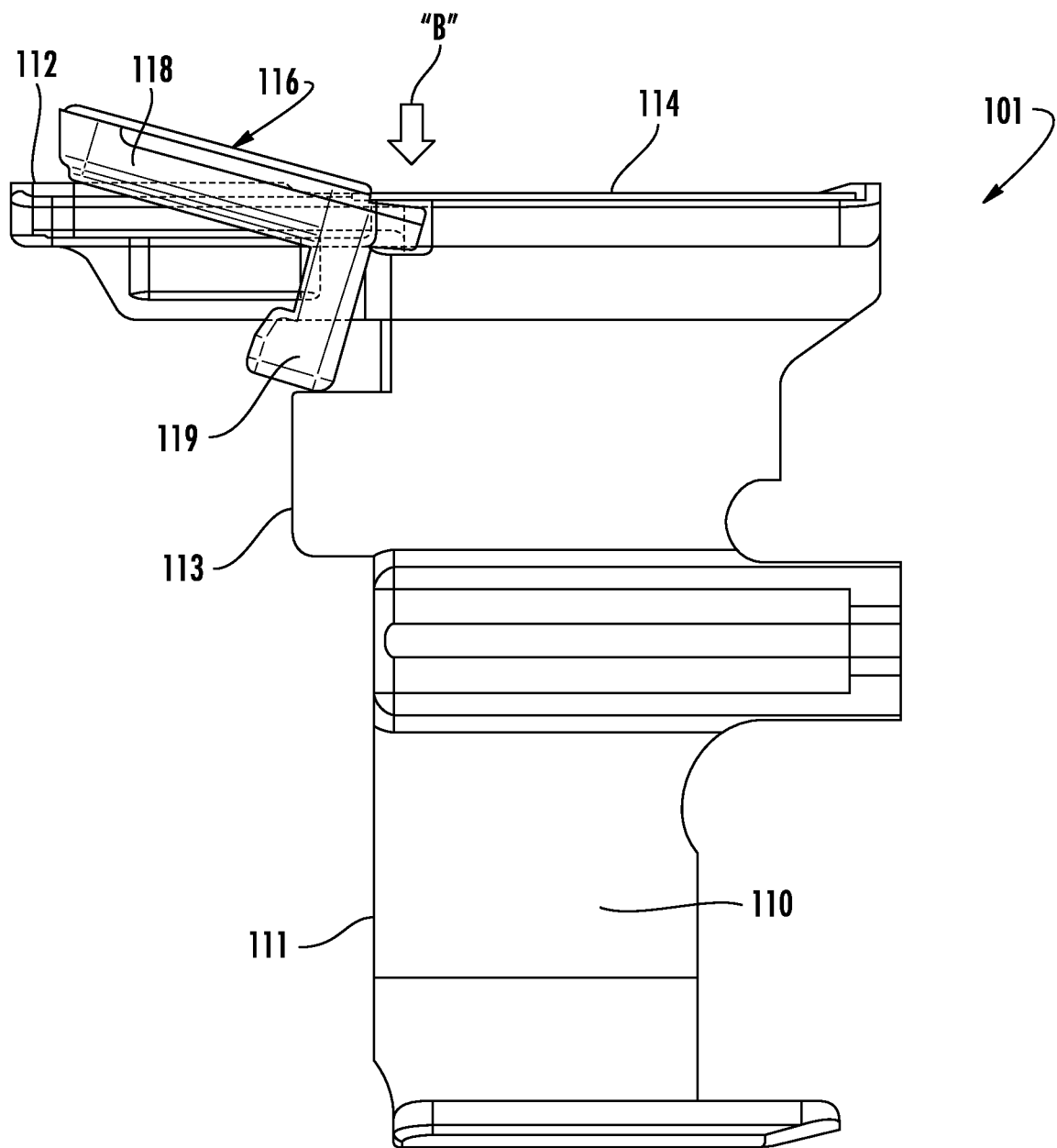
FIG. 2 depicts a side view of a drive assembly in accordance with an embodiment of the present disclosure.

FIG. 2 shows an illustrative drive assembly 101 for a surgical stapling instrument, including drive member 110, spring 114, and lockout member 116.

Drive member 110 may be any structure capable of pushing at least one of a shuttle or a knife of a surgical stapling instrument with the necessary force to effectively sever or staple human tissue. Drive member 110 may be an I-beam, an E-beam, or any other type of drive member capable of performing similar functions. In the embodiment shown in FIG. 2, drive member 110 is an I-beam and includes a first flange 113a that travels in a channel 108 (see FIG. 3A) in the anvil jaw assembly 102, and a second flange 113b that travels in a channel 115 (see FIG. 5) in the staple jaw assembly 104. Spring 114 is mounted to the drive member 110 by any technique within the purview of those skilled in the art. In embodiments, spring 114 is welded to drive member 110 on upper face 112 of drive member 110. Spring 114 is configured to bias engagement portion 118 of locking member 116 in the direction of Arrow "B", urging engagement portion 118 to extend beyond upper face 112 of drive member 110 to enable the locking mechanism. Distal movement of drive assembly 101 advances shuttle 130 by contact with a lower distal end portion 111 of drive member 110 and advances knife 150 by contact with upper distal portion 113 of drive member 110.

Figure 3:
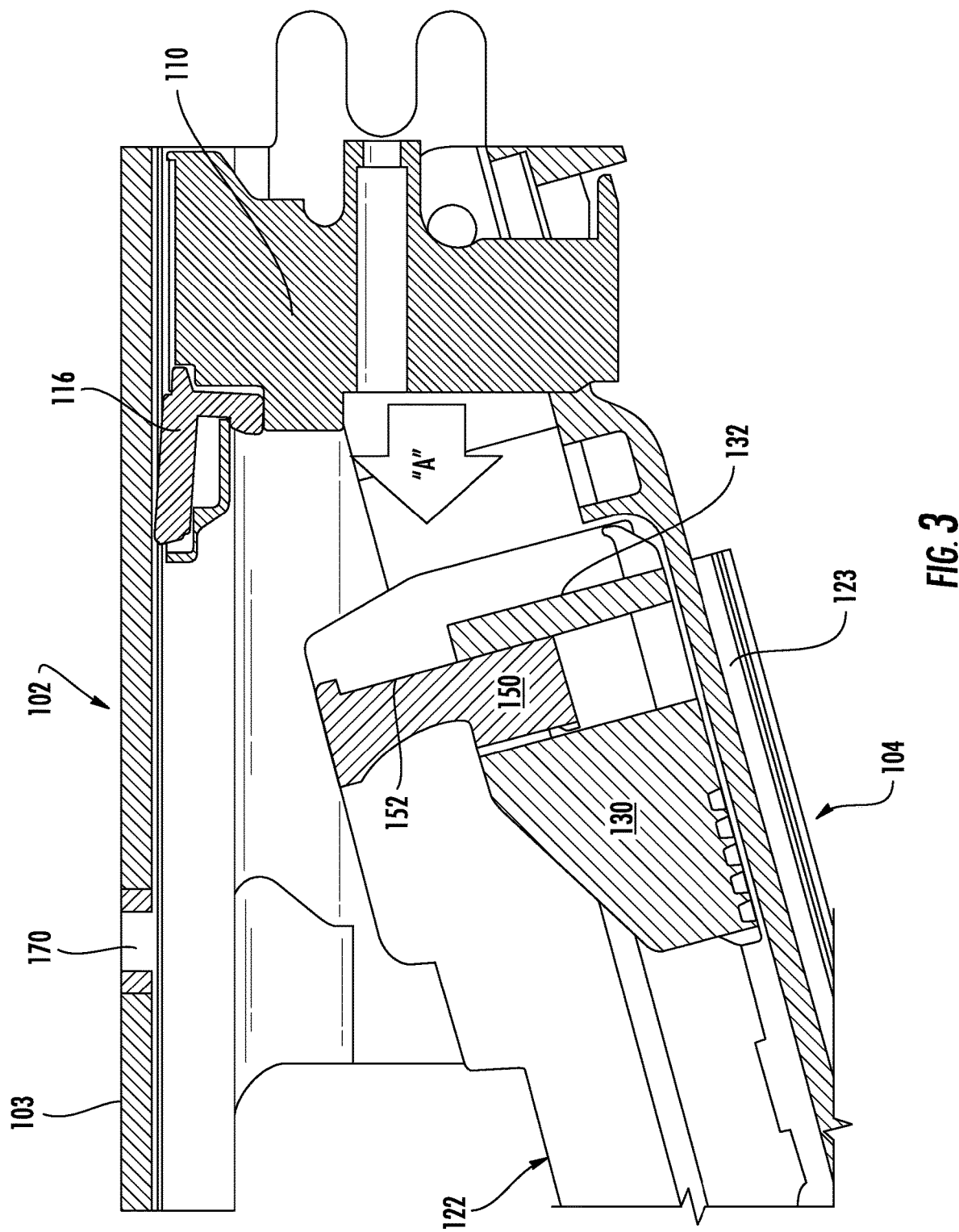
FIG. 3 is a partial side, cross-sectional view of a surgical stapling instrument including the drive assembly of FIG. 2, with the jaws of the end effector in the open position and a fresh reload positioned in the staple jaw assembly.
Figure 3A:
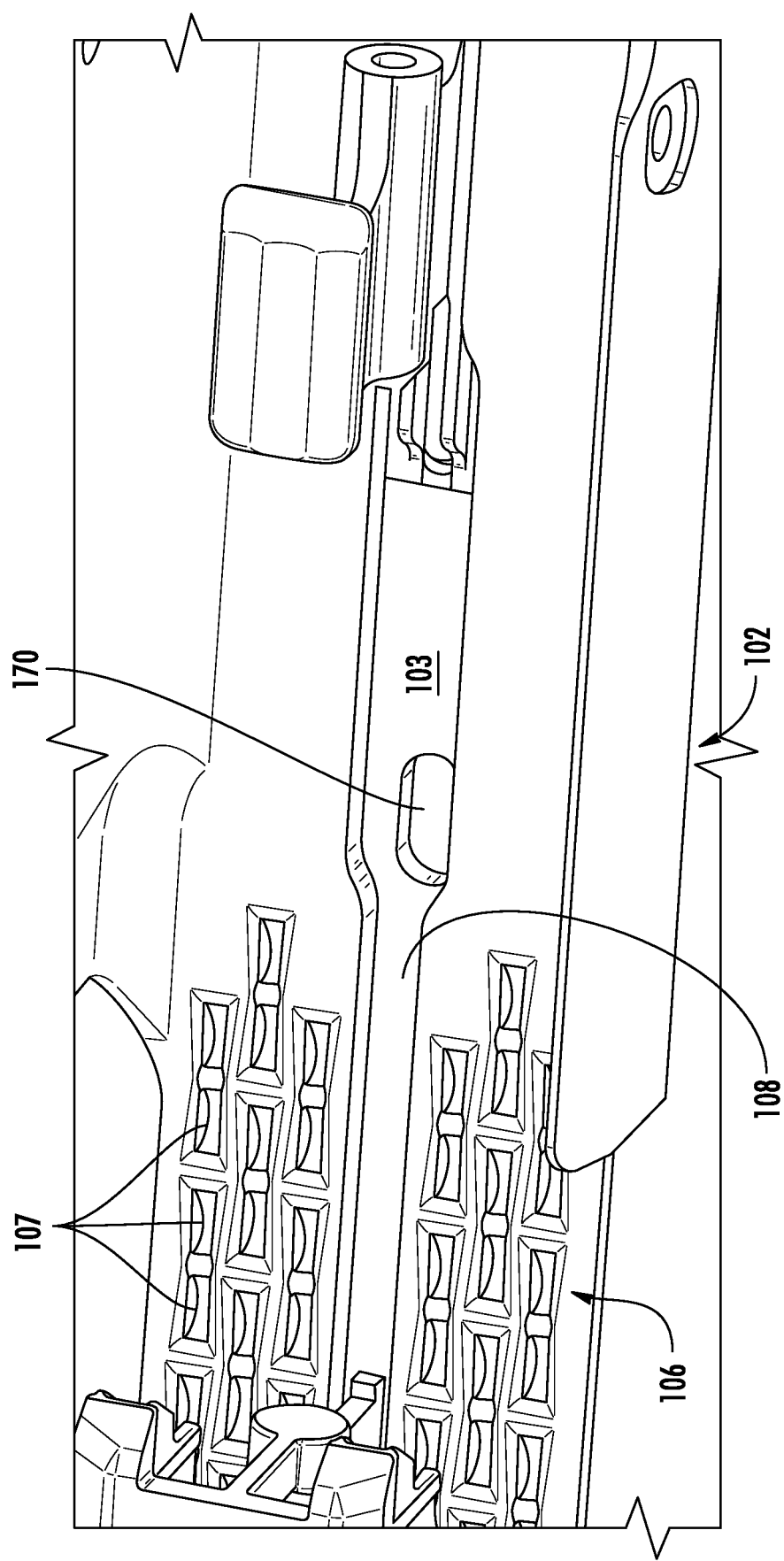
FIG. 3A is a perspective view of the anvil jaw assembly.

FIG. 3 shows the proximal end of a fresh reload 122 including shuttle 130 and knife 150 loaded into jaw 123 while jaw assemblies 102, 104 are in the open position. In FIG. 3, drive member 110 is in the proximal home position of the surgical stapling instrument.

Figure 5:
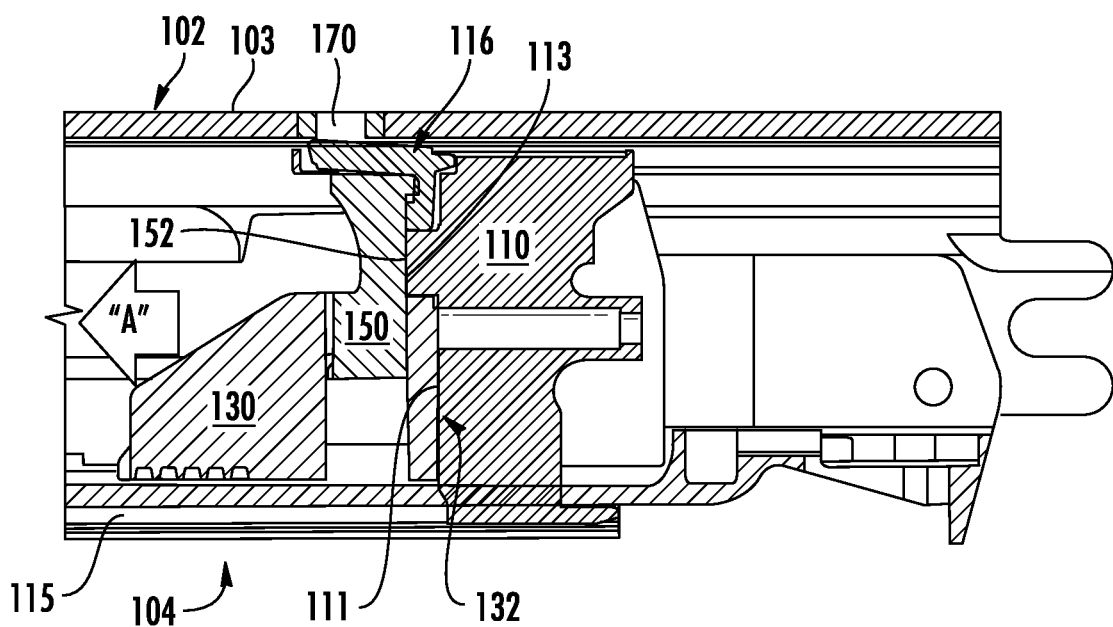
FIG. 5 is a partial side, cross-sectional view of the surgical stapling instrument of FIG. 3 with the jaw assemblies of the end effector in the closed position and the drive assembly partially advanced distally.

Once the jaw assemblies 102, 104 are approximated to grasp tissue, knife 150 engages a footer 119 of locking member 116 overcoming the bias of spring 114, keeping engagement portion 118 at or below upper face 112 of drive member 110, disabling the locking mechanism and permitting locking member 116 to bypass slot 170 formed in jaw assembly 102 as the drive member moves distally, as best seen in FIG. 5. Locking member 116 is generally L-shaped. Slot 170 is located on jaw assembly 102 in a position proximal of staple forming pockets 107 of anvil 106 (see FIG. 3A).

Figure 4:
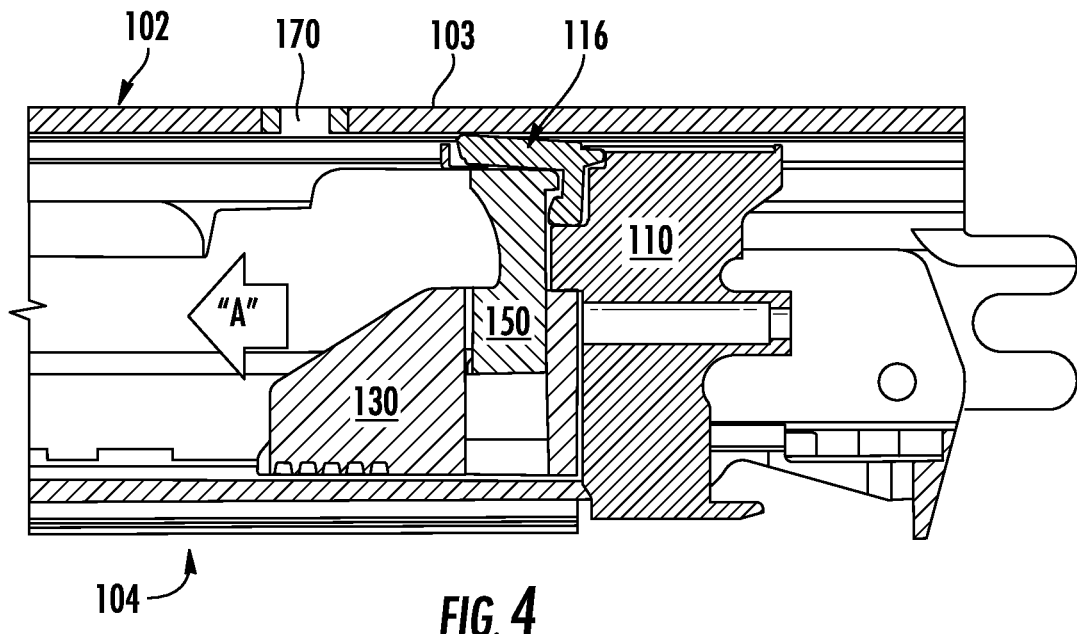
FIG. 4 is a partial side, cross-sectional view of the surgical stapling instrument of FIG. 3 with the jaw assemblies of the end effector in the closed position and the drive assembly in the home position.

In FIG. 4, the fresh reload is shown in place. The proximal end 132 of shuttle 130 is engaging lower distal end portion 111 of drive member 110 so that drive member 110 drives shuttle 130 distally upon firing. Similarly, a proximal portion 152 of knife 150 engages an upper distal portion 113 of drive member 110 so that knife 150 may be driven distally. In FIG. 5, drive member 110 continues to drive shuttle 130 and knife 150 distally. Because knife 150 engages footer 119 of locking member 116, locking member 116 is maintained in a first position and unable rotate upwardly to interact with slot 170, permitting continued distal translation of drive member 110 through a complete firing stroke.

Figure 6:
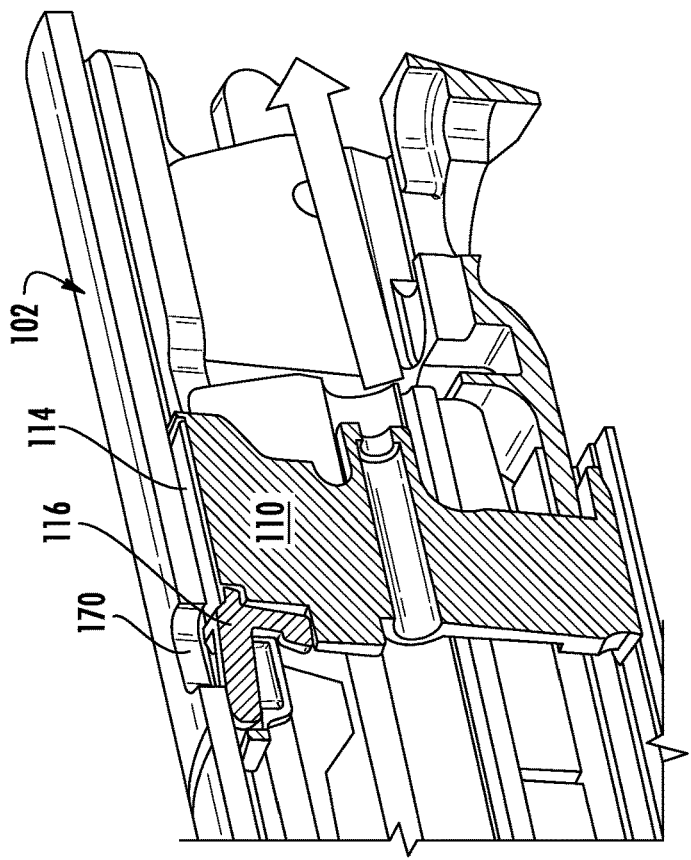
FIG. 6 is a partial side, cross-sectional view of a surgical stapling instrument of FIG. 3 with the jaws of the end effector in the closed position and the drive assembly moved proximally after completion of a firing stroke and ejection of staples from the staple cartridge.

Once drive member 110 translates distally through a complete firing stroke during which stapling and severing of tissue have occurred, drive member 110 can be retracted, leaving shuttle 130 and knife 150 parked at a position in a distal portion of cartridge 122. In embodiments, shuttle 130 may be unable to move proximally towards the home position due to friction with cartridge 122. In embodiments, knife 150 may be parked in a predetermined position in a distally located garage 165 (not shown), the garage 165 including lateral surfaces that face the cutting tip of knife 150. As drive member 110 is retracted, despite the biasing force of spring 114, engagement portion 118 of locking member 116 is unable to rotate upward as it is blocked by contact with surface 103 of upper jaw assembly 102, as shown in FIG. 6.

Figure 7:
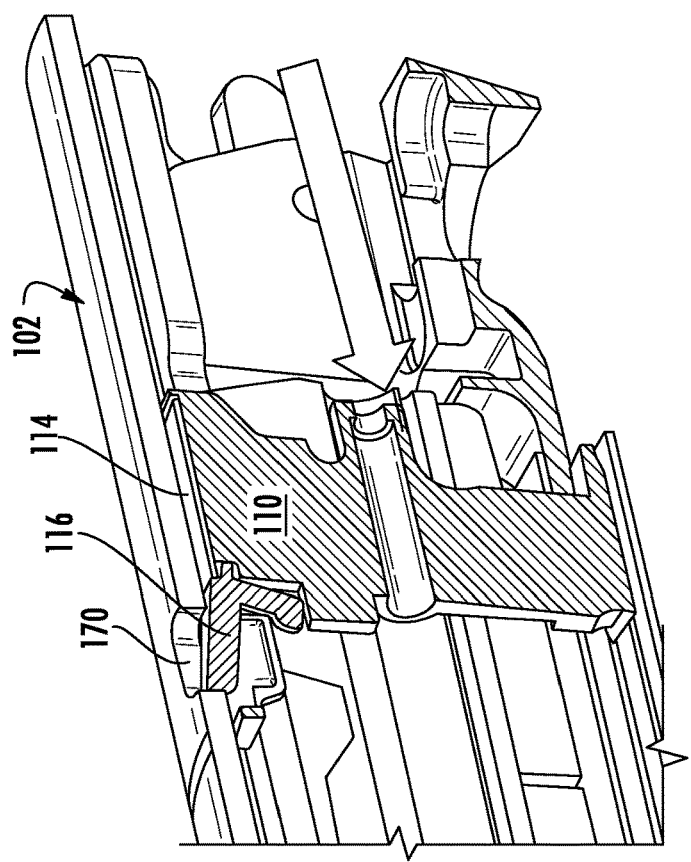
FIG. 7 is a partial side, cross-sectional view of a surgical stapling instrument of FIG. 3 with the jaws of the end effector in the closed position with a spent cartridge in place in the lower jaw assembly, thereby activating the lockout mechanism.

Further retraction of drive member 110 positions locking member 116 proximal of slot 170. Because the staple cartridge is spent and there is no knife to restrain movement of locking member 116, any attempt to re-fire the surgical stapling instrument will be prevented by the rotation of locking member 116, under the bias of spring 114, above upper surface 112 of drive member 110 and into slot 170, as seen in FIG. 7.

Figure 8:
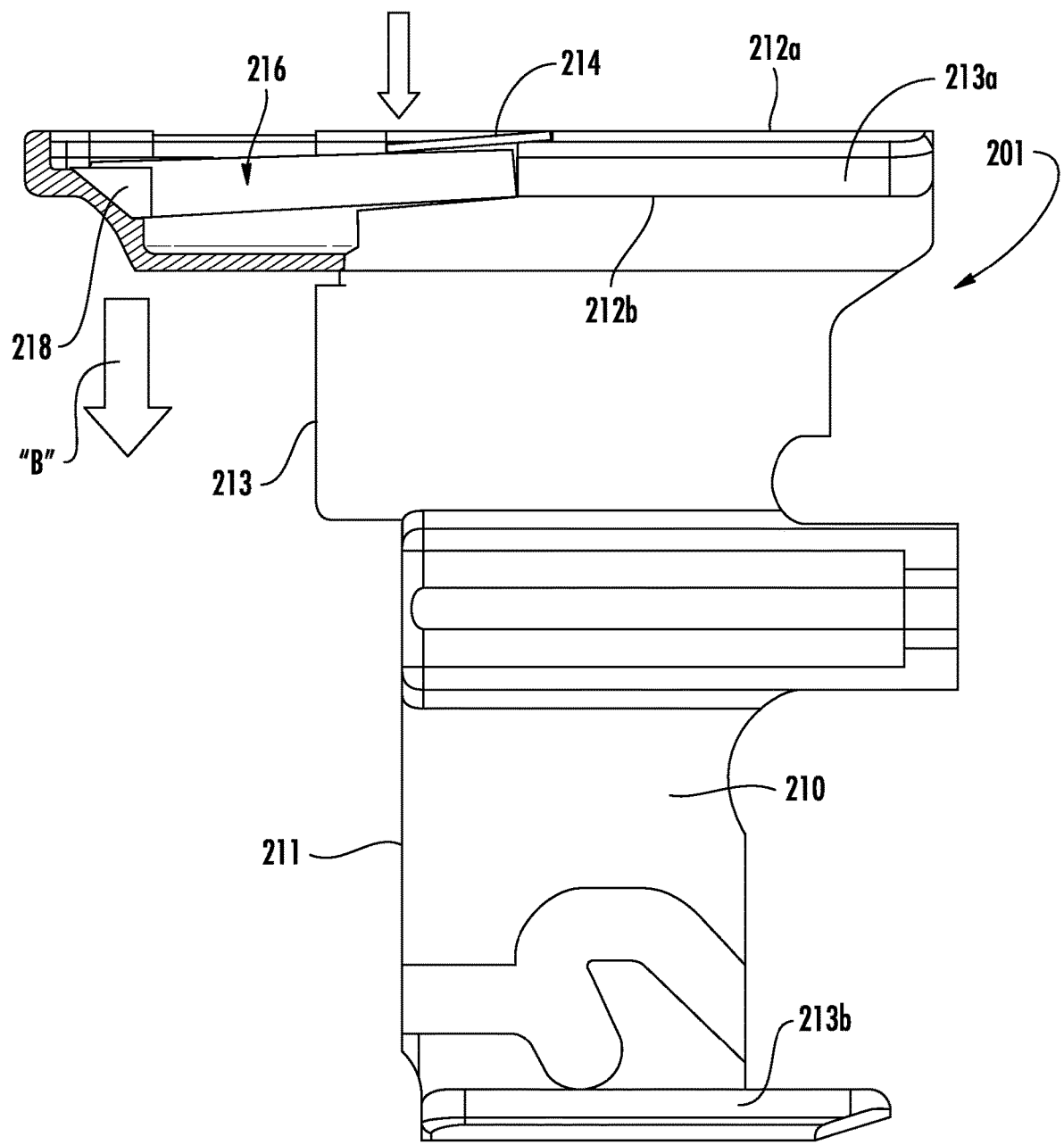
FIG. 8 depicts a side view of a drive assembly in accordance with another embodiment of the present disclosure.

FIG. 8 shows an alternative embodiment of a driver assembly 201 for a surgical stapling instrument, including drive member 210, spring 214, and lockout member 216.

Drive member 210 may be any structure capable of pushing at least one of a shuttle or a knife of a surgical stapling instrument with the necessary force to effectively sever and/or staple human tissue. As shown, drive member 210 is an I-beam and includes a first flange 213a that travels in a channel 208 (see FIG. 9) in the anvil jaw assembly 202, and a second flange 213b that travels in a channel 215 (see FIG. 9) in the staple jaw assembly 204. Spring 214 is welded to upper face 212a drive member 210. Spring 214 is configured to bias engagement portion 218 of locking member 216 in the direction of Arrow "B", urging engagement portion 218 to rotate below lower face 212b of drive member 210 to enable the locking mechanism. In this embodiment, locking member 116 is substantially linear.

In operation, distal movement of drive assembly 201 advances shuttle 230 by contact with lower distal end portion 211 of drive member 210 and advances knife 250 by contact with upper distal portion 213 of drive member 210.

Figure 9:
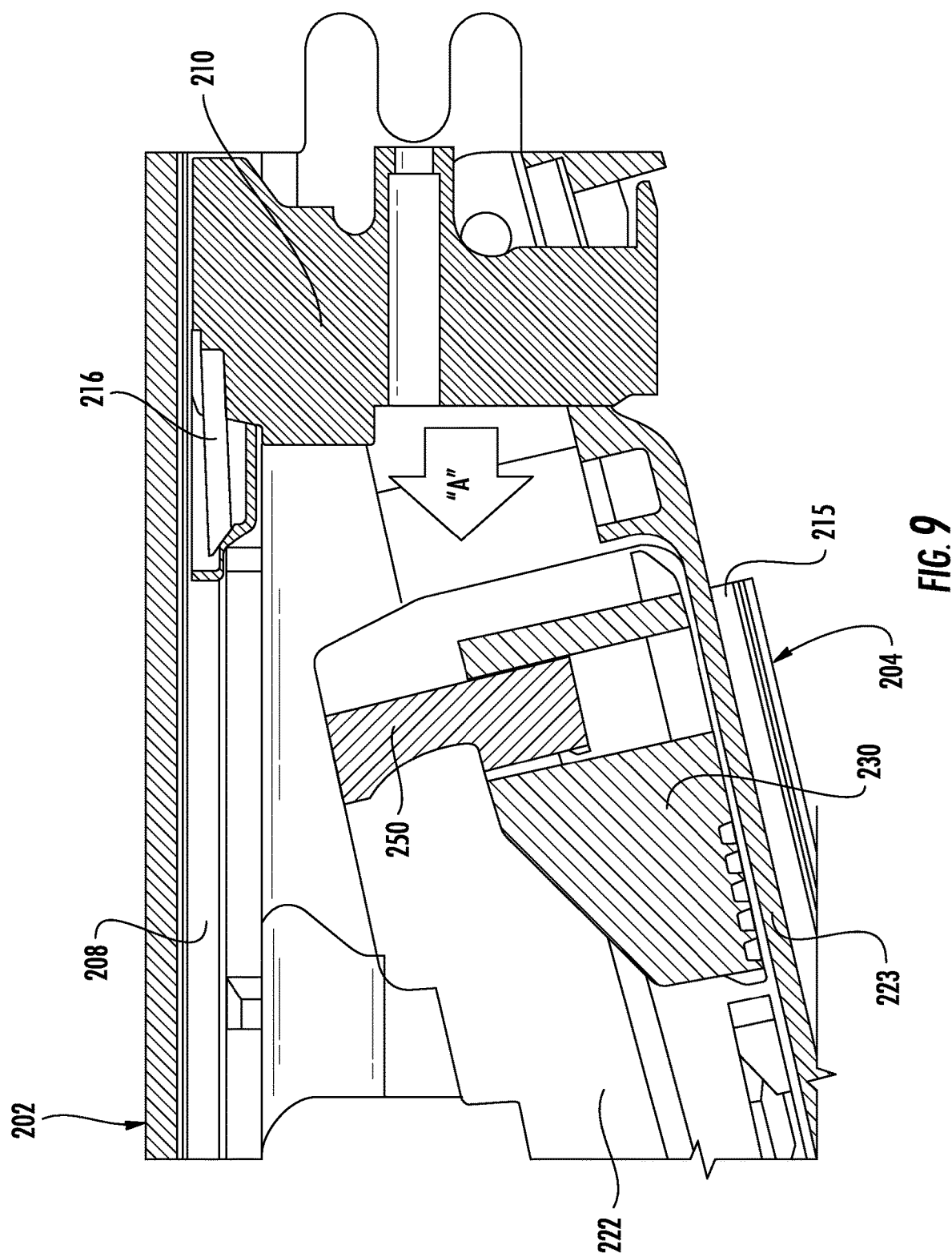
FIG. 9 is a partial side, cross-sectional view of a surgical stapling instrument including the drive assembly of FIG. 8, with the jaws of the end effector in the open position and a fresh reload positioned in the staple jaw assembly.

FIG. 9 shows the proximal end of a fresh reload 222 including shuttle 230 and knife 250 loaded into jaw 223 while the jaw assemblies 202, 204 are in the open position. In FIG. 9, drive member 210 is in the proximal home position of the surgical stapling instrument.

Figure 10:
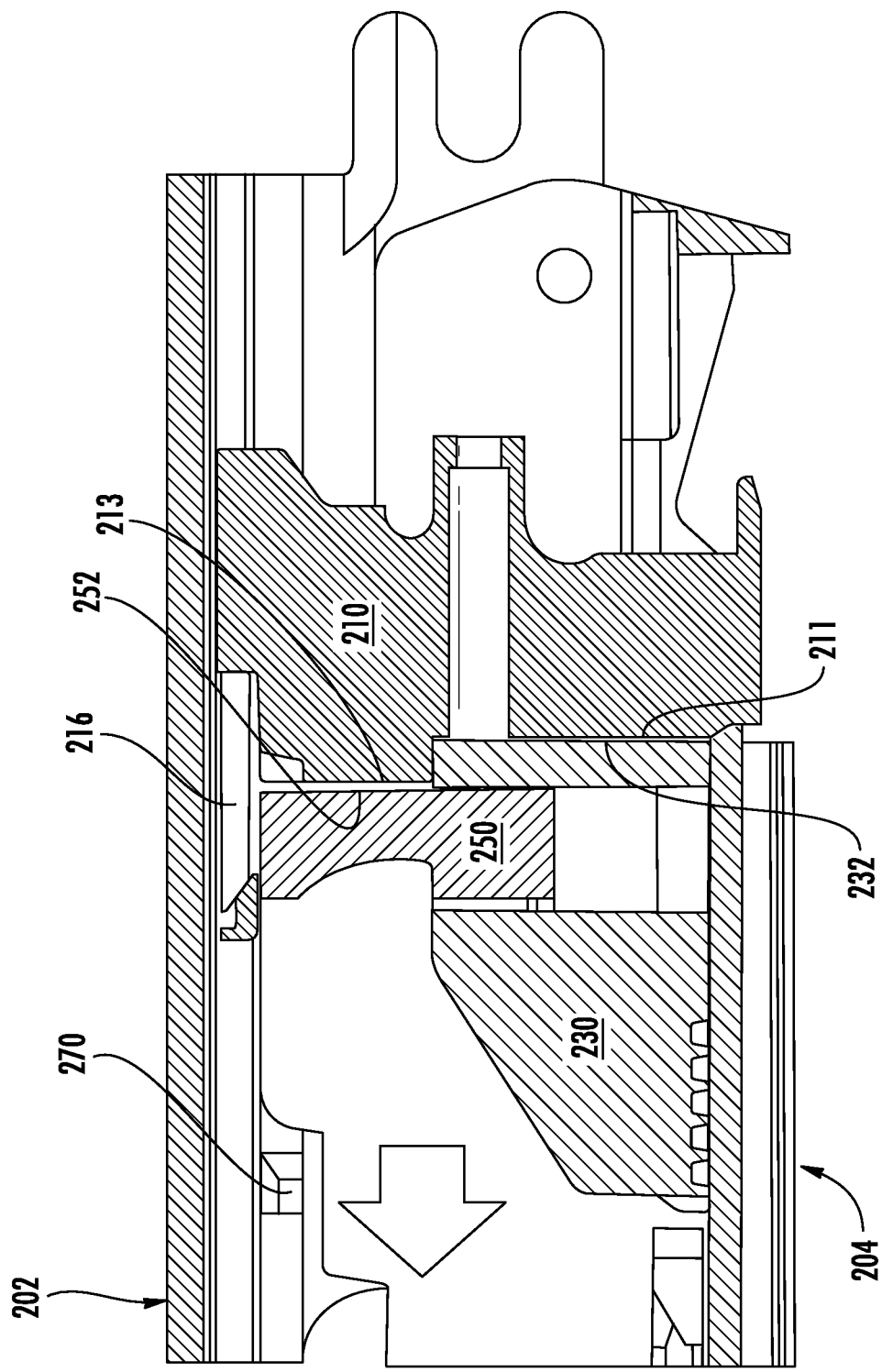
FIG. 10 is a partial side, cross-sectional view of the surgical stapling instrument of FIG. 9 with the jaw assemblies of the end effector in the closed position and the drive assembly in the home position.

Once the upper and lower jaw assemblies are in position to grasp tissue, knife 250 engages locking member 216 overcoming the bias of spring 214, keeping engagement portion 218 aligned with lower face 212b of drive member 210, permitting locking member 216 to bypass a pocket 270 formed in a lower surface of channel 208 of jaw assembly 202 as the drive member moves distally, as best seen in FIG. 10.

Figure 11:
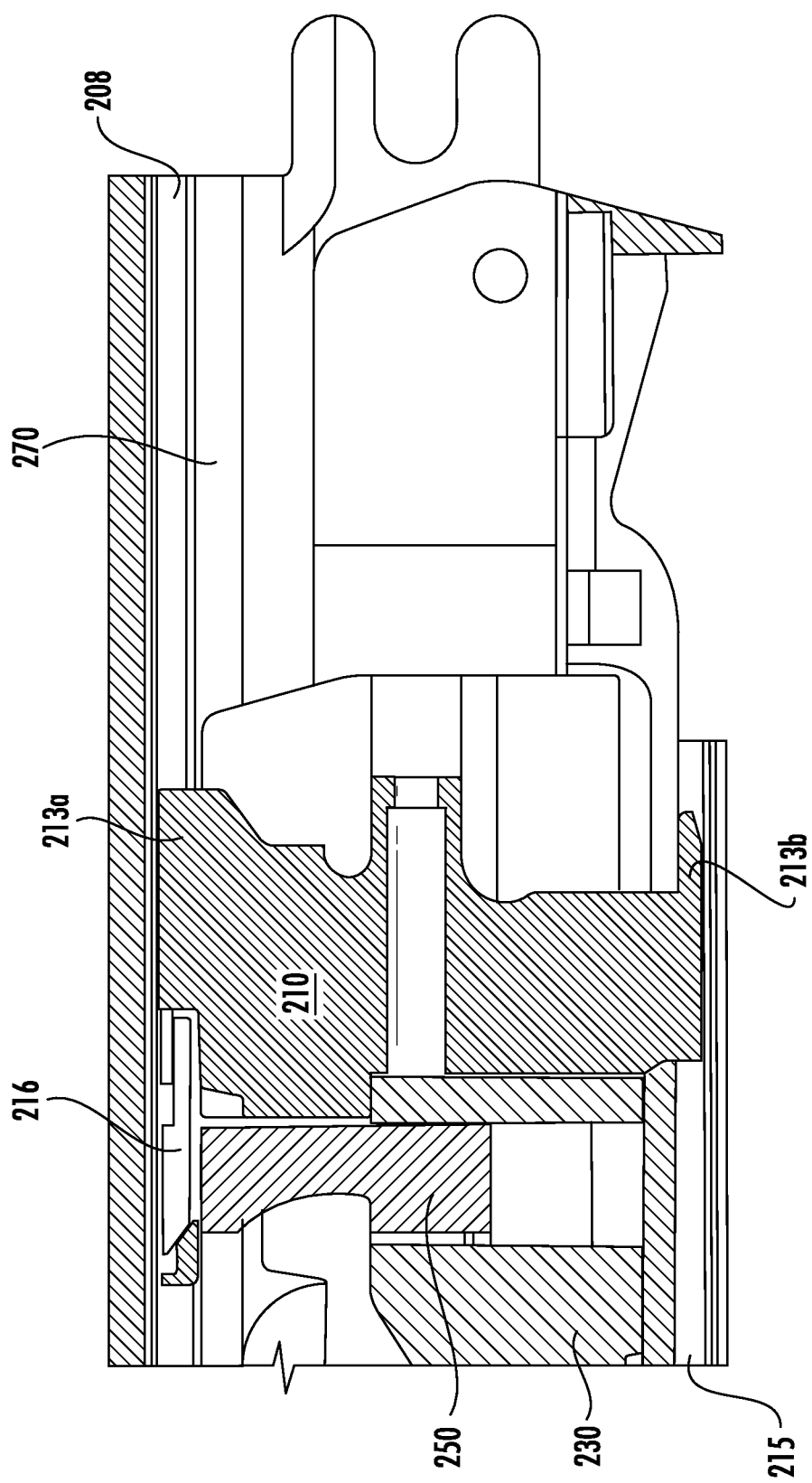
FIG. 11 is a partial side, cross-sectional view of the surgical stapling instrument of FIG. 9 with the jaw assemblies of the end effector in the closed position and the drive assembly partially advanced distally.

In FIG. 10, the fresh reload is in place. The proximal end 232 of shuttle 230 engages a lower-distal portion 211 of drive member 210 so that drive member 210 drives shuttle 230 distally upon firing. Similarly, a proximal portion 252 of knife 250 engages an upper distal portion 213 of drive member 210 so that knife 250 may be driven distally. As drive member 210 continues distally, because knife 250 engages locking member 216, locking member 216 is maintained in a first position and unable rotate downwardly to interact with pocket 270 (see FIG. 11), and the locking mechanism is disengaged, permitting continued distal translation of drive member 210 through a complete firing stroke.

Figure 12:
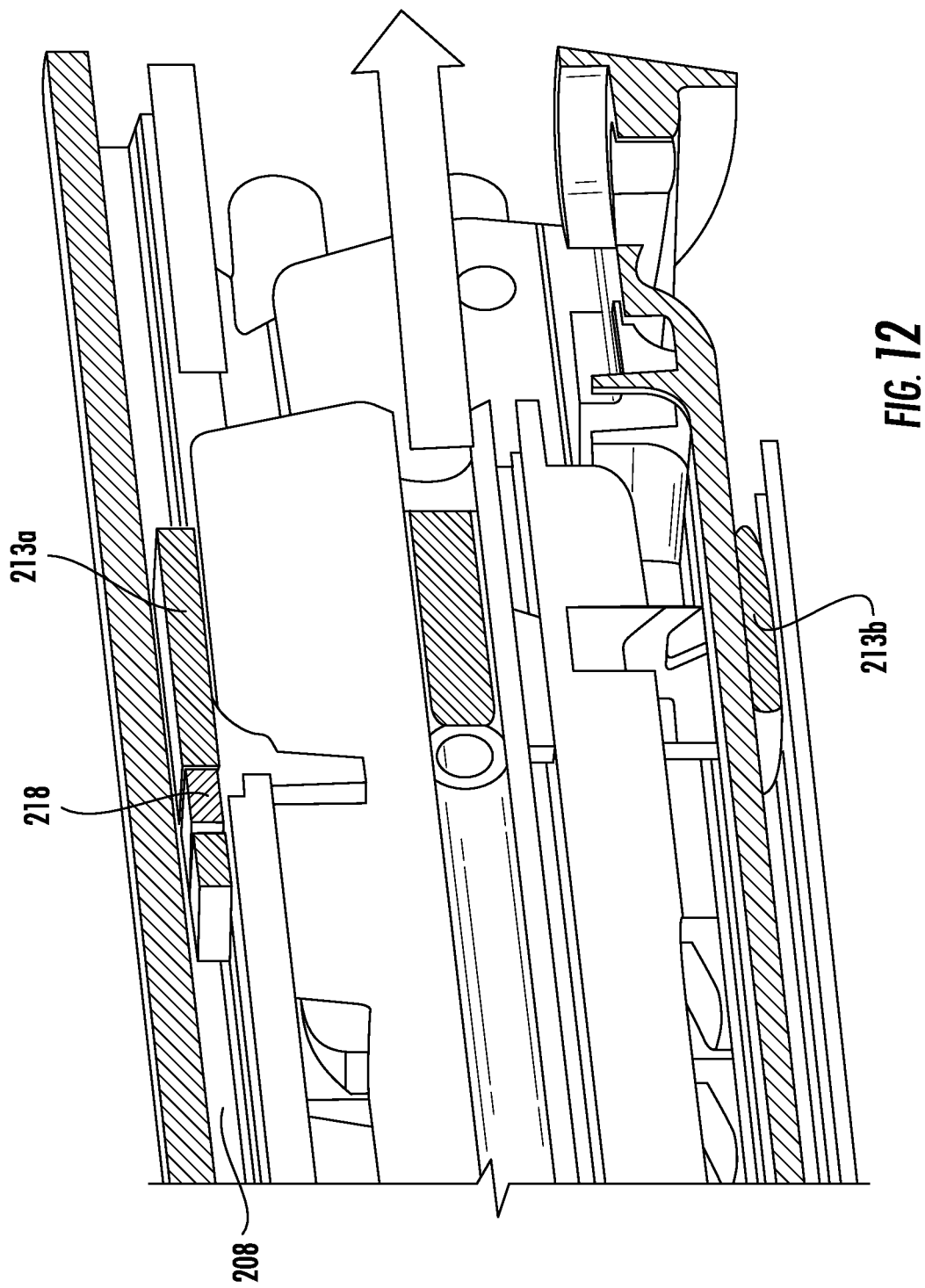
Figure 13:
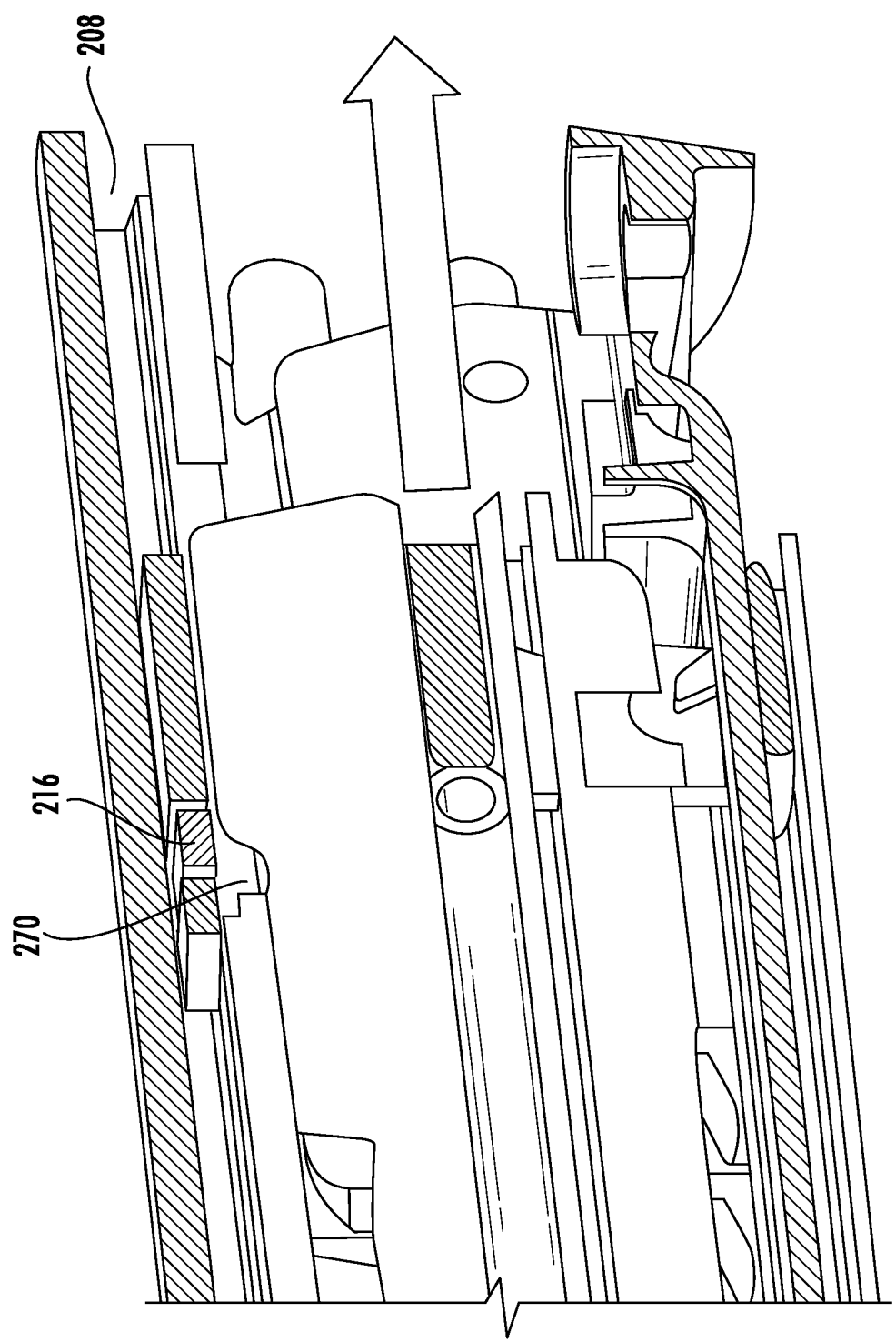

Once drive member 210 translates distally through a complete firing stroke and severing and stapling of tissue have occurred, drive member 210 can be retracted, leaving shuttle 230 and knife 250 at a parked position in a distal portion of cartridge 222. As drive member 210 is retracted, despite the biasing force of spring 214, engagement portion 218 of locking member 216 is unable to rotate downward as it rides along the lower surface of channel 208 of jaw assembly 202 as shown in FIG. 12. Once locking member reaches slot 270, it may rotate downwardly as shown in FIG. 13, but such rotation will not interfere with proximal motion of drive member 210.

Once further retraction of drive member 210 positions locking member 216 proximal of pocket 270 (see FIG. 14), because the staple cartridge is spent and there is no knife to restrain downward movement of locking member 216, any attempt to re-fire the surgical stapling instrument will be prevented by activation of the locking mechanism when locking member 216 rotates under the bias of spring 214, downwardly below surface 212b of drive member 210 and into contact with notch 271 of pocket 270 as seen in FIG. 15.

Figure 16:
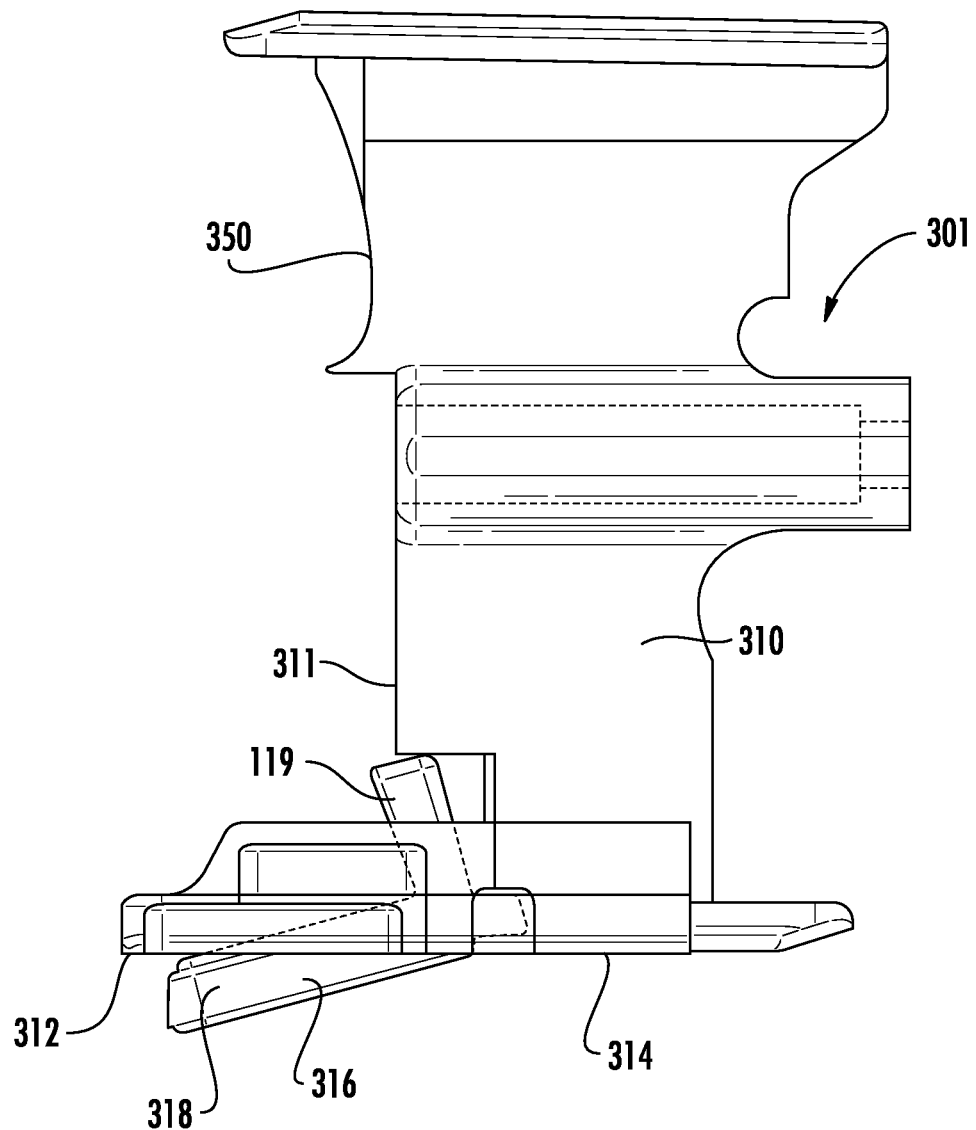
FIG. 16 depicts a side view of a drive assembly in accordance with another embodiment of the present disclosure.
Figure 17:
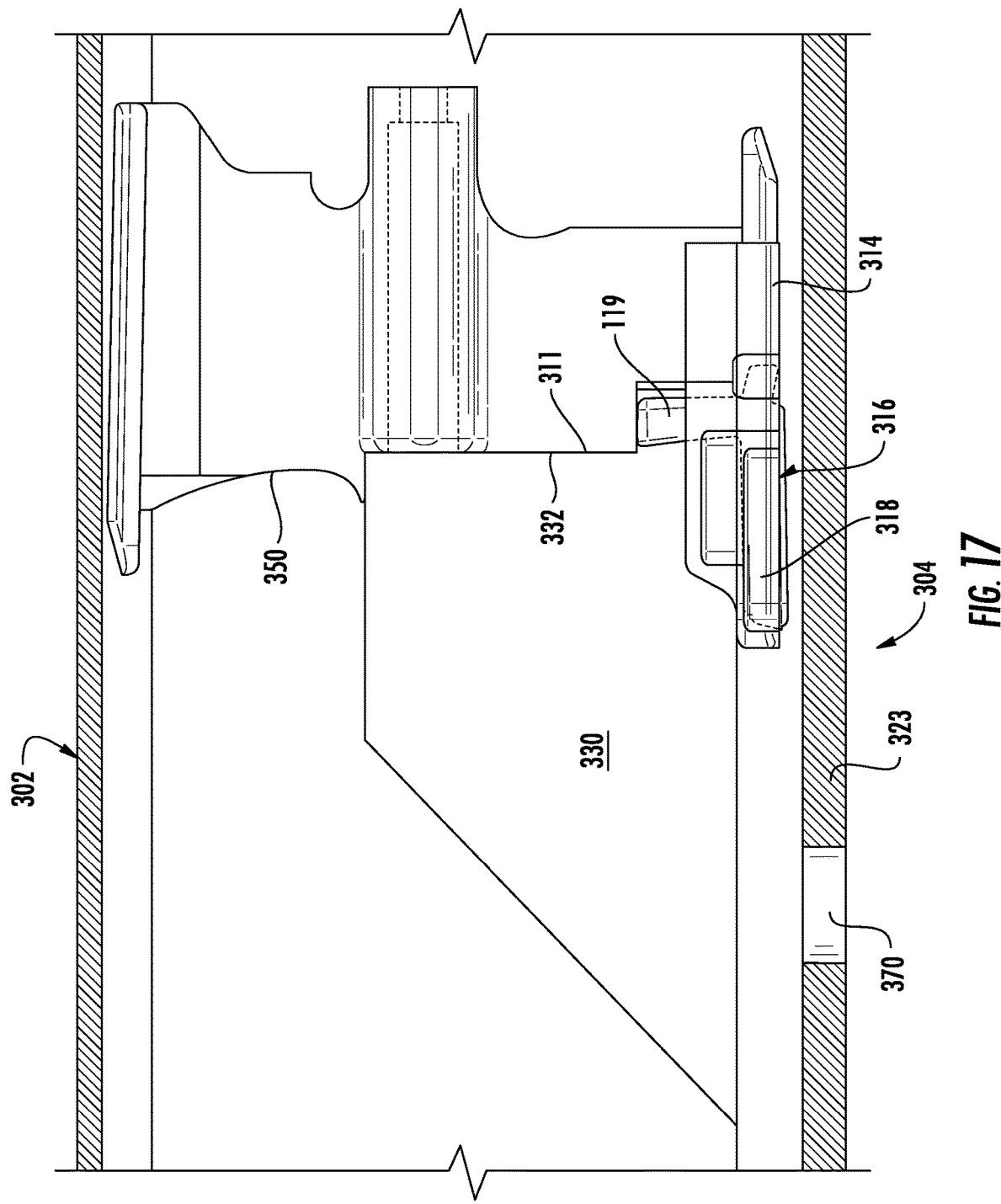
FIG. 17 is a partial side, cross-sectional view of a surgical stapling instrument including the drive assembly of FIG. 16 with the jaw assemblies of the end effector in the closed position and the drive assembly in the home position.

FIGS. 16 and 17 depict an alternative embodiment of a drive assembly 301 for use with a surgical stapling instrument. In this embodiment, shuttle 330 maintains locking member 316 out of engagement with slot 370 in staple jaw assembly 304 (rather than a slot in the anvil jaw assembly), thereby allowing knife 350 to be mounted to, or a sharpened surface of, drive member 310.

Specifically, as seen in FIG. 16, drive assembly 301 includes drive member 310, spring 314, and lockout member 316. In this embodiment, spring 314 is configured to bias engagement portion 318 of locking member 316 in the direction of Arrow "B", urging engagement portion 318 to rotate below lower face 312 of drive member 310 to enable the locking mechanism.

In FIG. 17, with a fresh reload in place, proximal end 332 of shuttle 330 engages a lower-distal portion 311 of drive member 310 so that drive member 310 drives shuttle 330 distally upon firing. Because shuttle 330 also engages portion 319 of locking member 216, locking member 316 is maintained in a first position and unable rotate downwardly to interact with slot 370, permitting distal translation of drive member 310 through a complete firing stroke. Unlike previously presented illustrative embodiments where the knife disables the locking mechanism, in this embodiment shuttle 330 is responsible for disabling the locking mechanism. Using shuttle 330 to restrain rotation of locking member 316 allows for knife 350 to be mounted to or formed directly on drive member 310, reducing cartridge cost.

Once drive member 310 translates distally through a complete firing stroke and severing and stapling of tissue have occurred, drive member 310 can be retracted, leaving shuttle 330 at a parked position at a distal portion of the cartridge. Further retraction of drive member 310 positions locking member 316 proximal of pocket 370. Because the staple cartridge is spent and there is no shuttle to restrain downward movement of locking member 316, any attempt to re-fire the surgical stapling instrument will be prevented by activation of the locking mechanism when locking member 316 rotates under the bias of spring 314, downwardly below surface 312 of drive member 310 and into contact with pocket 370 in essentially the same manner as described above.

Figure 18:
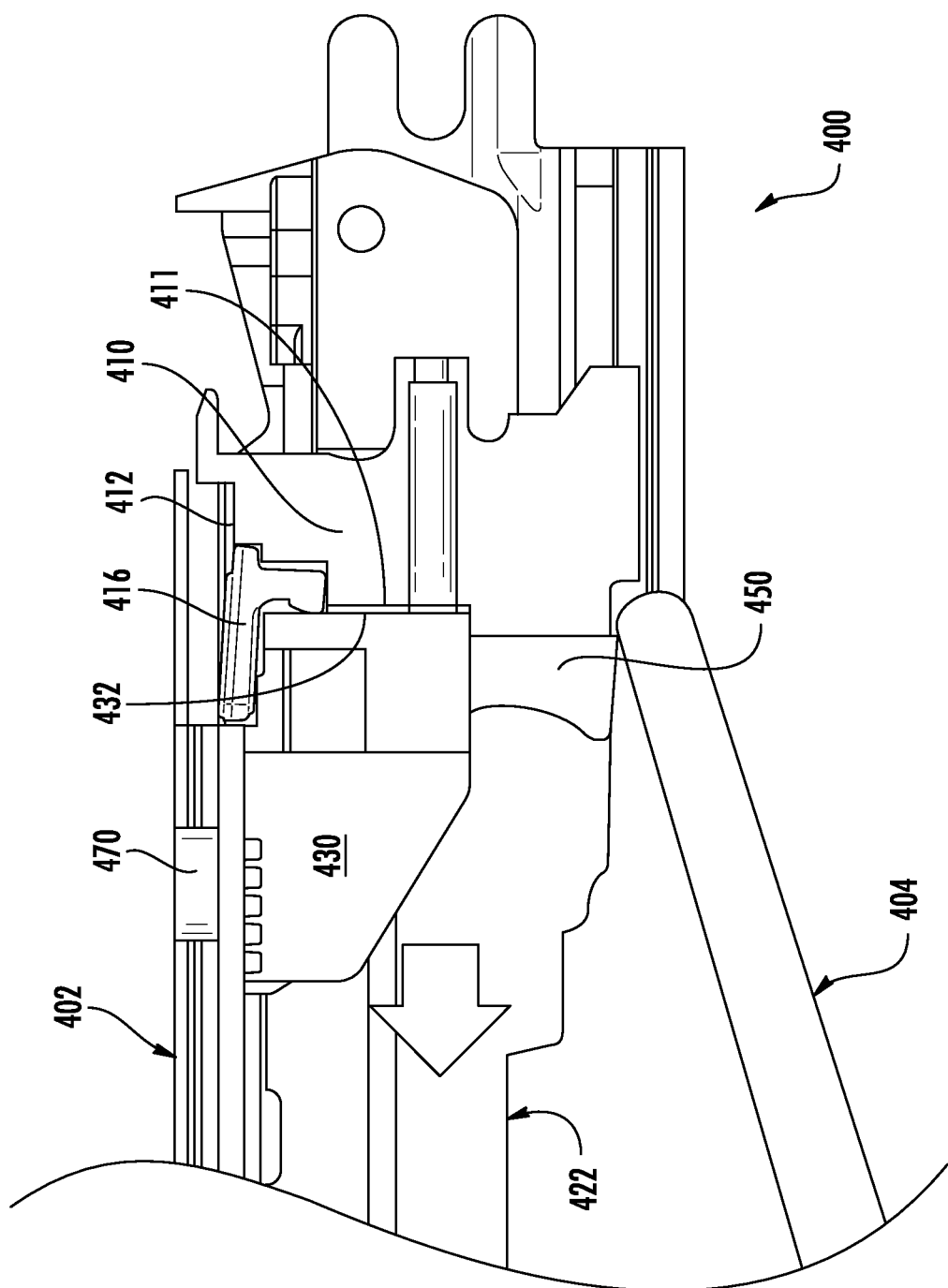
FIG. 18 is a partial side, cross-sectional view of a surgical stapling instrument including another illustrative embodiment of a drive assembly, with the jaws of the end effector in the open position and a fresh reload positioned in the staple jaw assembly.
Figure 19:
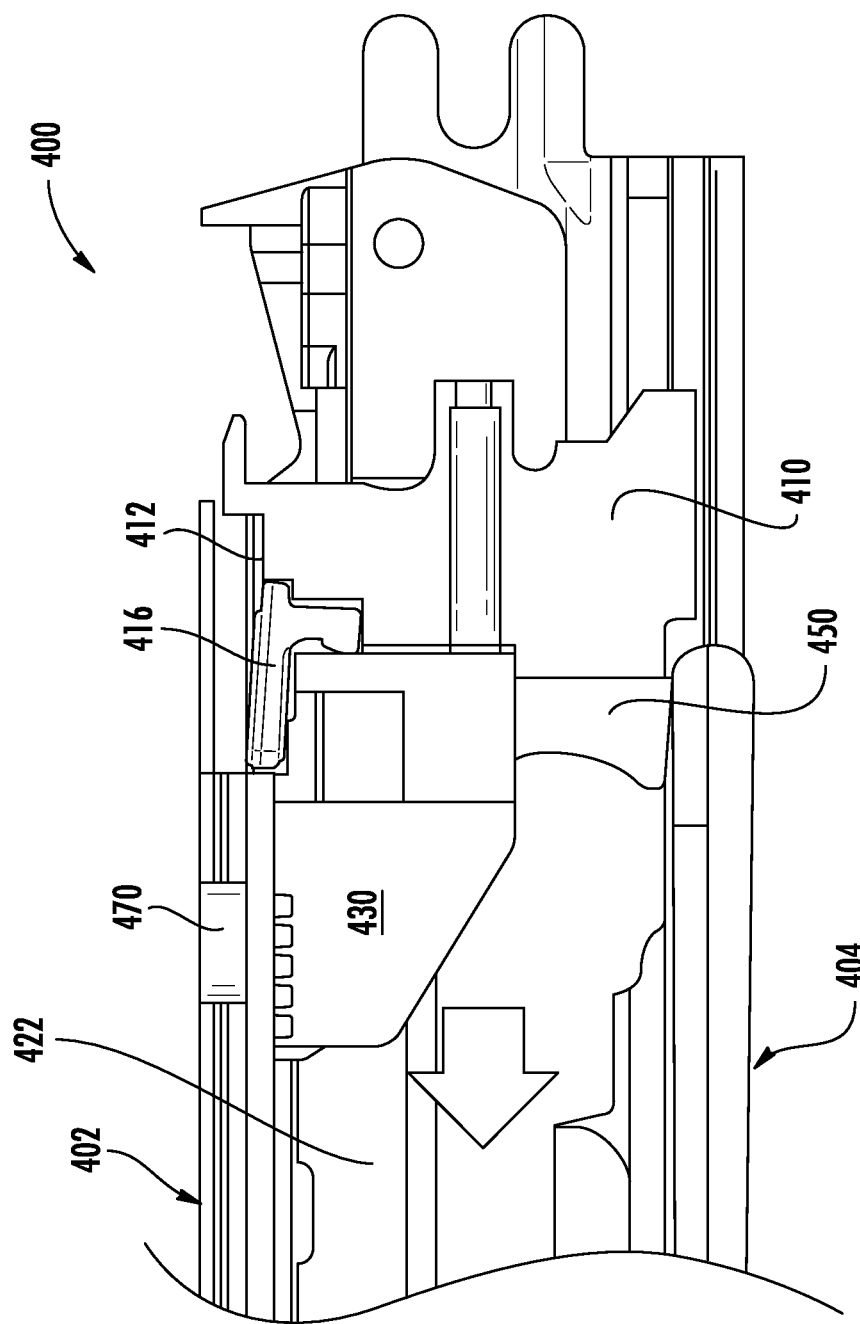
FIG. 19 is a partial side, cross-sectional view of the surgical stapling instrument of FIG. 18 with the jaw assemblies of the end effector in the closed position and the drive assembly in the home position.

FIGS. 18 and 19 show an alternative embodiment of a surgical stapling instrument 400 in accordance with the present disclosure. Surgical stapling instrument 400 includes a movable anvil jaw assembly 404 and a stationary staple jaw assembly 402 which are configured to move between an open position to a closed position. In the open position, a fresh staple cartridge 422 can be loaded into stationary staple jaw assembly 402, a spent staple cartridge removed from stationary staple jaw assembly 402, and tissue may be positioned between the jaw assemblies 402, 404. In the closed position, jaw assemblies 402, 404 cooperate to close upon and clamp tissue such that cartridge 422 and anvil 406 are in close cooperative alignment. Unlike the previously described embodiments, in surgical stapling instrument 400 the jaw containing cartridge 422 is stationary and the jaw assembly containing the anvil pivots to the open position.

FIG. 18 shows the proximal end of a fresh reload 422 including shuttle 430 loaded into stationary jaw assembly 402 while the jaw assemblies 402, 404 are in the open position. Knife 450 may be mounted to drive member 410, or it may be a sharpened surface of drive member 410, or a component of cartridge 422, either independent of, or mounted to shuttle 430.

With a fresh reload in place and the jaw assemblies 402, 404 in the closed position (see FIG. 18), proximal end 432 of shuttle 430 engages upper portion 411 of drive member 410, disabling the locking mechanism so that drive member 410 drives shuttle 430 distally upon firing. Because shuttle 430 also engages locking member 416, locking member 416 is maintained in a first position and unable rotate upwardly to interact with a slot 470 in stationary jaw assembly 402, permitting distal translation of drive member 410 through a complete firing stroke.

Once drive member 410 translates distally through a complete firing stroke and severing and stapling of tissue have occurred, drive member 410 can be retracted, leaving shuttle 430 at a parked position at a distal portion of the cartridge. Further retraction of drive member 410 positions locking member 416 proximal of pocket 470. Because the staple cartridge is spent and there is no shuttle to restrain movement of locking member 416, any attempt to re-fire the surgical stapling instrument will be prevented by activation of the locking mechanism when locking member 416 rotates under the bias of spring 414, upwardly above surface 412 of drive member 410 and into contact with pocket 470 in essentially the same manner as described above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical instrument comprising:
an elongate shaft with an end effector having first and second jaws;
a release member movably coupled to one of the first and second jaws;
a drive member configured to translate relative to the end effector;
a locking member movable from a first position permitting distal translation of the drive member, to a second position preventing distal translation of the drive member;
a slot configured to engage the locking member when the locking member is in the second position; and
wherein the release member is configured to disengage from the locking member after the drive member has been driven distally.

2. The surgical instrument of claim 1, wherein the release member, when proximally positioned, is configured to releasably engage the locking member to maintain the locking member in the first position.

3. The surgical instrument of claim 1, wherein the first jaw comprises an anvil jaw assembly and the second jaw comprises a staple jaw assembly including a removable staple cartridge.

4. The surgical instrument of claim 3, further comprising a knife housed within the removable staple cartridge, wherein the knife comprises the release member.

5. The surgical instrument of claim 3, further includes a shuttle having a distal inclined portion housed within the removable staple cartridge, wherein the shuttle comprises the release member.

6. The surgical instrument of claim 3, wherein the slot resides in the anvil jaw assembly.

7. The surgical instrument of claim 1, wherein the drive member further includes a first flange configured to translate through a channel in the first jaw, and a second flange configured to translate through a channel in the second jaw.

8. The surgical instrument of claim 1, wherein the locking member is generally L-shaped.

9. The surgical instrument of claim 1, wherein the locking member is substantially linear.

10. The surgical instrument of claim 1, further comprising a spring configured to bias the locking member towards the second position.

11. The surgical instrument of claim 1, further comprising an actuator in contact with the drive member and configured to translate the drive member distally through the end effector, wherein the actuator includes a control device of a robotic surgical system.

12. A surgical instrument comprising:
an elongate shaft with an end effector having first and second jaws;
a release member movably coupled to one of the first and second jaws;
a drive member configured to translate relative to the end effector;
a locking member movable from a first position permitting distal translation of the drive member, to a second position preventing distal translation of the drive member, wherein the locking member is biased towards the second position; and
wherein the release member, when proximally positioned, is configured to releasably engage the locking member to maintain the locking member in the first position, and configured to disengage from the locking member after the drive member has been driven distally.

13. The surgical instrument of claim 12, further comprising a slot configured to engage the locking member when the locking member is in the second position.

14. The surgical instrument of claim 12, wherein the first jaw comprises an anvil jaw assembly and the second jaw comprises a staple jaw assembly including a removable staple cartridge.

15. The surgical instrument of claim 14, further comprising a knife housed within the removable staple cartridge, wherein the knife comprises the release member.

16. The surgical instrument of claim 14, further includes a shuttle having a distal inclined portion housed within the removable staple cartridge, wherein the shuttle comprises the release member.

17. The surgical instrument of claim 14, wherein the slot resides in the anvil jaw assembly.

18. The surgical instrument of claim 12, wherein the locking member is generally L-shaped.

19. The surgical instrument of claim 12, wherein the locking member is substantially linear.

20. The surgical instrument of claim 12, further comprising an actuator in contact with the drive member and configured to translate the drive member distally through the end effector, wherein the actuator includes a control device of a robotic surgical system.

* * * * *